(12) United States Patent
Dalton et al.

(10) Patent No.: US 6,812,003 B2
(45) Date of Patent: Nov. 2, 2004

(54) COMPOUNDS AND METHODS FOR MODULATING CELL-ADHESION MEDIATED DRUG RESISTANCE

(75) Inventors: William S. Dalton, Tampa, FL (US); Jason S. Damiano, Tampa, FL (US); Anne E. Cress, Tucson, AZ (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 10/024,017

(22) Filed: Dec. 21, 2001

(65) Prior Publication Data

US 2003/0078210 A1 Apr. 24, 2003

Related U.S. Application Data

(63) Continuation of application No. 09/795,484, filed on Mar. 1, 2001.
(60) Provisional application No. 60/186,198, filed on Mar. 1, 2001.

(51) Int. Cl.[7] .................................................. C12P 21/06

(52) U.S. Cl. ............................ 435/69.1; 514/4; 514/14; 514/15; 514/16; 514/17; 514/18; 530/317; 530/326; 530/327; 530/328; 530/329; 530/330; 530/331

(58) Field of Search ............................... 514/4, 14, 15, 514/16, 17, 18; 530/317, 326, 327, 328, 329, 330, 331

(56) References Cited

PUBLICATIONS

Dermer "Another Anniversary for the war on cancer" 1994, Biotechnology, vol. 12, pp. 320.*

Voskoglou–Nomikos, Clinical predictive valus of the in vitro cell line, human xenograft, and mouse allograft preclinical cancer models, Clinical Cancer Research, vol. 9, (11) Sep. 2003, pp. 4227–4239.*

Damiano et al., J.S., "Cell Adhesion Mediated Drug Resistance (CAM–DR): Role of Integrins and Resistance to Apoptosis in Human Myeloma Cell Lines," *Blood*, vol. 93, No. 5 (Mar. 1999), pp. 1658–1667.

Pennington et al., M.E., "The Use of a Combinatorial Library Method to Isolate Human Tumor Cell Adhesion Peptides," *ESCOM Science Publishers: Molecular Diversity*, vol. 2 (1996), pp. 19–28.

(List continued on next page.)

*Primary Examiner*—Christopher Tate
*Assistant Examiner*—Roy Teller
(74) *Attorney, Agent, or Firm*—Saliwanchik, Lloyd & Saliwanchik

(57) ABSTRACT

Peptides and methods of their use for inhibiting drug and radiation-therapy resistance in cancerous cells in which efficacy of chemotherapy and/or radiotherapy of a patient is enhanced by administration of an effective amount of a peptide that inhibits cell adhesion mediated drug resistance (CAM-DR). Preferably, the peptide comprises D-amino acids having the sequence:

kmviywkag                                    (RZ-3)

or is a variant or modified version thereof. The peptide is preferably administered to the patient prior to chemotherapy and/or radiation therapy. Inhibition of cell adhesion mediated drug resistance (CAM-DR) by RZ-3 in multiple myeloma cells is disclosed.

17 Claims, 29 Drawing Sheets

PUBLICATIONS

Hazlehurst et al., L.A., "Adhesion to Fibronectin via μ1 Integrins Regulates p27$^{kp1}$ Levels and Contributes to Cell Adhesion Mediated Drug Resistance (CAM–DR)," *Oncogene*, (Nov. 2001), pp. 011/012–003/012.

DeRoock et al., I.B., *Synthetic Peptides Inhibit Adhesion of Human Tumor Cells to Extracellular Matrix Proteins*[1], *Cancer Research*, vol. 61 (Apr. 2001), pp. 3308–3313.

* cited by examiner a.

a.

b.

A.

B.

Two Different Forms of Tumor-Microenvironment Interactions Influence Drug Response in Cancer A. Soluble form of tumor-microenvironment interaction (IL-6)
B. Direct contact form of tumor-microenvironment interaction (ECM)

COMPOUNDS AND METHODS FOR MODULATING CELL-ADHESION MEDIATED DRUG RESISTANCE

CROSS-REFERENCE TO A RELATED APPLICATION

This application is a continuation of U.S. application Ser. No. 09/795,484, filed Mar. 1, 2001, which claims the benefit of U.S. Provisional Application Ser. No. 60/186,198, filed Mar. 1, 2000.

GOVERNMENT SUPPORT

The subject matter if this application has been supported by a research grant from the National Institutes of Health under grant number R01 CA77859. Accordingly, the government may have certain rights in this invention.

FIELD OF THE INVENTION

The present invention relates to the use of pharmaceutical agents to modulate cell-adhesion. In particular, the invention relates to the use of peptides for inhibiting cell-adhesion and enhancing the efficacy of the chemotherapeutic and/or radiation treatments in the treatment of cancer.

BACKGROUND OF THE INVENTION

Cell adhesion is a complex process that is important for maintaining tissue integrity and generating physical and permeability barriers within the body. Cell adhesion is mediated by specific cell surface adhesion molecules (CAMs). There are many different families of CAMs, including the immunoglobulin, integrin, selectin and cadherin superfamilies, and each cell type expresses a unique combination of these molecules.

Although cell adhesion is required for certain normal physiological functions including wound repair, there are situations in which cell adhesion is undesirable. For example, many pathologies, such as metastasis, autoimmune diseases, and inflammatory diseases, involve abnormal cellular adhesion. Cell adhesion may also play a role in graft rejection. In such pathologies, modulation of cell adhesion may be desirable.

Multiple Myeloma and Treatment Resistance

Multiple myeloma is an incurable malignancy of the plasma cell characterized by migration and localization to the bone marrow where cells then disseminate and facilitate the formation of bone lesions. Despite initial responses to chemotherapy, myeloma patients ultimately develop drug resistance and become unresponsive to a wide spectrum of anticancer agents, a phenomenon known as multidrug resistance (MDR). The development of resistance to front-line chemotherapeutic drugs, such as melphalan (an alkylating agent) and doxorubicin (an anthracycline), is a major factor responsible for treatment failure; thus, the median survival of 3.5 years has remained largely unchanged for the past three decades.

There are many potential mechanisms for drug resistance in myeloma including reduction in intracellular drug accumulation due to overexpression of MDR1/Pglycoprotein, alterations in drug targets such as topoisomerase II, enhanced DNA repair, and overexpression of anti-apoptotic proteins such as bcl-2. These mechanisms are chiefly due to alterations in the malignant cell itself and can be studied using in vitro human myeloma cell. However, these mechanisms alone cannot account for all drug resistance, nor are they likely to explain cell survival following initial cytotoxic drug exposure. Additional mechanisms conferring low level drug resistance are believed to play important roles in the survival and expansion of the malignant cell population. Recent studies have demonstrated that certain resistance mechanisms are observed only in vivo, suggesting that interactions between malignant cells and the surrounding microenvironment may be important in determining response to chemotherapeutic drug. Factors that allow for tumor cell survival following initial drug exposure need to be identified because these factors may eventually allow for expression of genes associated with acquired drug resistance. In addition, through understanding the mechanism that suppresses drug-induced apoptosis as well as other mediators of drug resistance, improved therapies can be developed which interfere with, or inhibit the resistance.

It is known that intercellular interactions can contribute to tumor cell survival during exposure to cytotoxic stresses such as radiation. It is also known that certain resistance mechanisms may only be functional in vivo, where tumor cells continue to interact with environmental factors such as extracellular matrix (ECM) and cellular counter-receptors. For example, Teicher et al. showed that mammary tumors made resistant to alkylating agents in vivo are sensitized to cytotoxic drugs once removed from the animal, Tumor resistance to alkylating agents conferred by mechanisms operative only in vivo, Science 247:1457,1990. Adhesive interactions between same cell types are known to confer resistance to alkylating agents via alterations in cyclin dependent kinase inhibitors such as p27$^{kip1}$, although the cell surface molecules mediating this type of kinetic resistance have yet to be identified. In addition, adhesion to ECM has been reported to induce P-glycoprotein expression and confer doxorubicin resistance in rat hepatocytes.

The integrin family of cellular adhesion molecules is a major class of receptors through which cells interact with extracellular matrix components (ECM). Recent evidence has implicated the integrins as being closely involved in the pathology of many diseases. Integrins have been shown to participate in intracellular signal transduction pathways that may contribute to tumor cell growth and survival.

Experimental evidence has implicated the PI integrins and fibronectin as playing a part in apoptotic suppression and cell survival. For example, Zhang et al. has demonstrated that fibronectin adhesion through $\alpha_5\beta_1$, (VLA-5) prevents cells from undergoing serum-starvation induced apoptosis by upregulating Bcl-2. The alpha 5 beta I integrin supports survival of cells on fibronectin and up-regulates Bcl-2 expression, Proc Natl Acad Sci USA 92(13):6161, 1995.

Similar observations are made by Scott et al. and Rozzo et al., who found that anti-$\beta_1$ antibodies and antisense oligonucleotides, respectively, enhanced chromatin condensation and nucleosomal DNA laddering, characteristics of cells committed to apoptosis. Fibronectin suppresses apoptosis in normal human melanocytes through an integrin-dependent mechanism, J Invest Dennaioi 108: 147, 1997. Induction of apoptosis in human neuroblastoma cells by abrogation of integrin mediated cell adhesion, Int J Cancer 70:688,–1997. PI integrin activation through interactions with ECM components such as fibronectin directly decreases DNA strand breaks in tumor derived endothelial cells exposed to a number of DNA damaging agents, including etoposide and ionizing radiation.

The $\alpha_4\beta_1$ (Very Late Activation Antigen 4, or VLA-4), $\alpha_5\beta_1$ (VLA-5), and $\alpha_4\beta_7$ heterodimers are the major fibronectin receptors of the integrin family. Although VLA-5 and $\alpha_4\beta_7$ expression are variable in most B cells during malignancy, VLA-4 is strongly expressed in myeloma cells collected from bone marrow. VLA-4 is unique among the integrins as it is the only heterodimer to have been shown to mediate cell-ECM as well as cell-cell interactions. VLA-4 binds to the CS-1 region of fibronectin as well as to vascular cell adhesion molecule-1 (VCAM-1) via separate binding sites. Adhesion to fibronectin via VLA-4 has been shown to prolong eosinophil survival and to downregulate FAS antigen expression, leading to a decrease in cell death. In early hematopoietic and germinal center B cells, adhesion to fibronectin or VCAM-1 via VLA-4 suppresses the apoptotic pathway and contributes to positive selection.

As myeloma cells adhere in the bone marrow, they stimulate their own growth and cause osteoclast formation through the increased synthesis and secretion of cytokines such as IL-1$\beta$, TNF-$\beta$, M-CSF, and IL-6. IL6, a potent growth factor for myeloma cells, is secreted from both tumor and stromal cells in response to co-adhesion and VLA-4 ligation. VLA-4 associates with or causes the phosphorylation f a number of signal transduction molecules, including CD19 receptor-associated protein tyrosine kinases and focal adhesion kinase (pp125$^{FAK}$, or FAK), which is an upstream activator of mitogen activated protein kinase (MAPK), among other proteins. FAK plays a major role in suppressing apoptosis both in adherent and suspension cells, and its cleavage by caspases early in the apoptotic process further emphasizes its importance within the cell.

Peptide and Cell-Adhesion

Peptides capable of modulating cell adhesion have been reported. U.S. Pat. No. 6,169,071 to Blaschuk, et al. discloses cyclic peptides comprising a cadherin cell adhesion recognition sequence HAV and methods for modulating cadherin-mediated cell adhesion in a variety of contexts. U.S. Pat. No. 6,020,460 to Pierschbacher, et al. disclosed conformationally stabilized synthetic Arg-Gly-Asp-containing peptides which have increased affinity and selectivity for the vitronectin receptor over that of linear, Arg-Gly-Asp-containing synthetic peptides. Such peptides are used to modulate cell-adhesion.

However, none of the above cited art references discloses or even suggests the administration of peptides to enhance chemo- or radiotherapy, nor in situations when such drugs may help to overcome cell adhesion inhibition-mediated drug resistance. In contrast, and teaching away from the instant application, the rise of drug resistant tumor cells is usually associated with reduced migratory and invasive ability and a lower adhesion capacity (see abstract by Scotlandi K. et al., Multidrug resistance and malignancy in human osteosarcoma, Cancer Res 1996 May 15;56(10):2434–9).

Accordingly, there is a need in the art for compounds that modulate cell adhesion to improve, for example, the efficacy of chemotherapy and radiation therapy of cancer cells such as multiple myeloma without the aforementioned disadvantages. The present invention fulfills this need and further provides other related advantages that will become apparent to one of ordinary skill of the art upon reading the following disclosure.

BRIEF SUMMARY OF THE INVENTION

It is therefore an aspect of the present invention to provide an improved protocol for the treatment of cancer.

It is a further aspect of the present invention to provide a protocol comprising the administration of pharmaceutical agents that disrupt cancer cell adhesion in vivo to enhance the efficacy of chemotherapeutic and/or radiation treatments.

It is a further aspect of the present invention to provide a protocol comprising the administration of peptides for inhibiting adhesion and thereby enhancing the efficacy of chemotherapeutic and/or radiation treatments in the treatment of cancer.

It is yet a further aspect of the present invention to provide a method of treating cancer that inhibits cell adhesion mediated drug resistance.

It is a further aspect of the present invention to provide a method that enhances the efficacy of cytotoxic drugs and/or radiation in the treatment of cancer.

In another embodiment, it is an aspect of the present invention to provide factors which confer cell adhesion mediated drug resistance, wherein such factors provide novel and specific targets for the development of therapies that can interfere with or inhibit cell adhesion mediated drug resistance.

It is a further aspect of the present invention to provide a rational connection between expression and function of the major integrin fibronectin receptors and the response to cytotoxic drugs in the human myeloma derived cell line RPMI 8226.

It is yet a further aspect of the present invention to provide changes in integrin expression and function in drug-resistant variants following chronic drug exposure that permit assessment of the effects of fibronectin on acute drug response in the drug sensitive parent line.

These and other aspects of the present invention will become obvious to those skilled in the art upon review of the following disclosure.

Adhesion of cancer cells to fibronectin via integrins or fibronectin interferes with drug and/or radiation induced apoptosis. Disclosed herein are specific agents that can interfere with cell adhesion mediated drug resistance and thereby enhance the ability of cytotoxic drugs and radiation to kill cancer cells. In particular, peptides are disclosed as a class of drugs that can block cell adhesion and prevent cell adhesion mediated drug resistance.

DETAILED DESCRIPTION OF THE DRAWINGS

Figure 1:
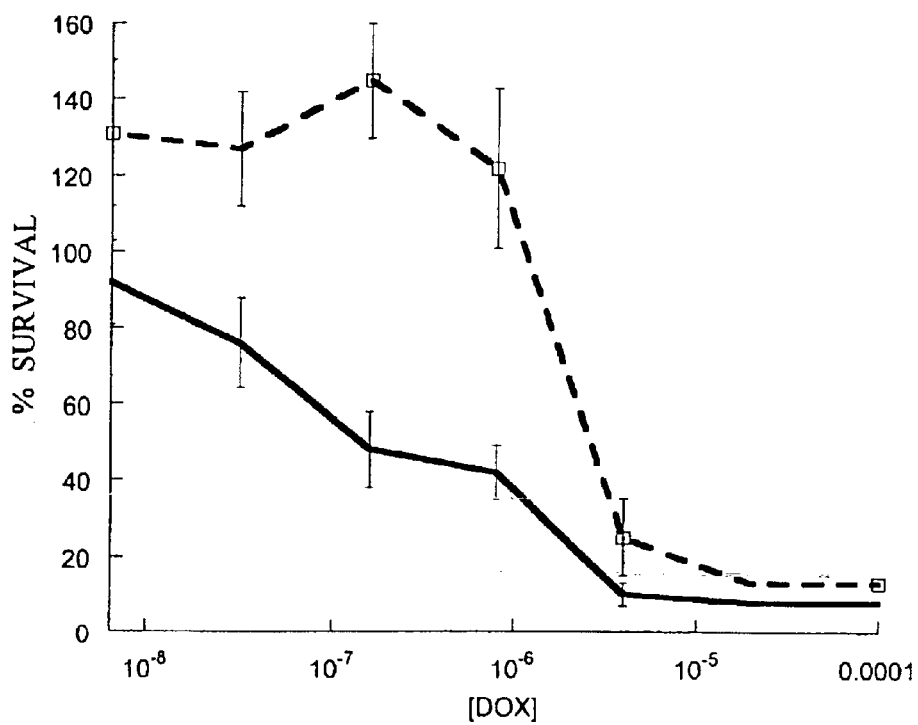
FIG. 1 illustrates 8226/S myeloma cells adhered to fibronectin (FN) having a survival advantage over non-adhered cells following acute doxorubicin exposure.
Figure 1:
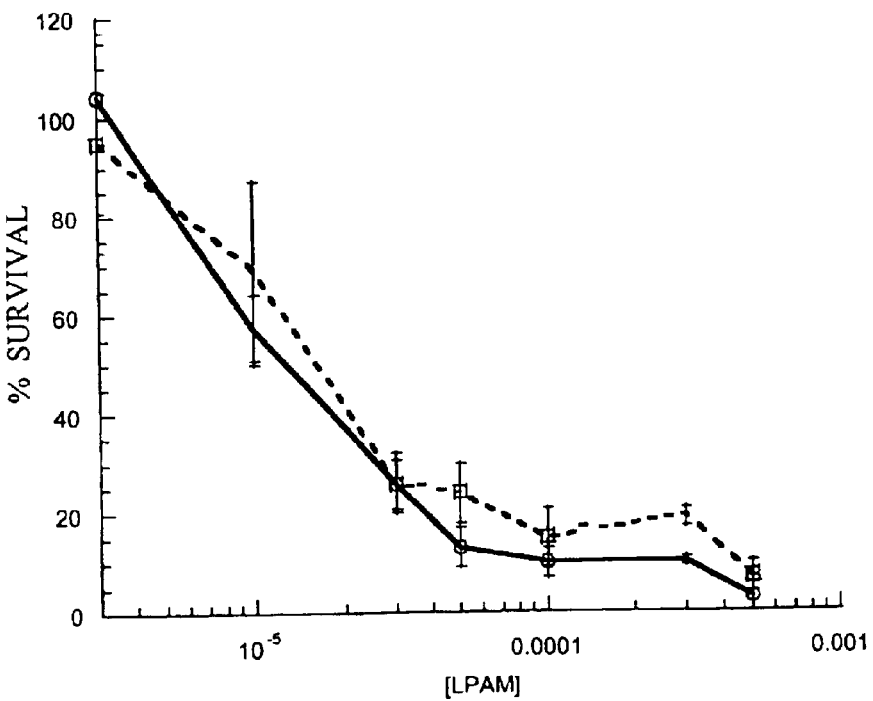

FIG. 1 illustrates 8226/S myeloma cells adhered to FN having a survival advantage over non-adhered cells following acute doxorubicin exposure (a) but not following melphalan exposure (b) in cell growth based cytotoxicity assays. FN-adhered cells (---) are bound to FN-coated plates 24 hours prior to one hour drug exposure and control cells are grown in suspension (—). Response to doxorubicin is 12.6 fold lower in FN-adhered cells compared to non-adhered controls (IC50 values for adhered and nonadhered cells are of $4.85 \times 10^{-7}$ M and $8.5 \times 10^{-8}$ M, respectively). Data points are presented as cell viability determined by MTT cytotoxicity assay compared to untreated controls. Graphs are representative experiments that are repeated 3 times in replicates of 4.

Figure 2:
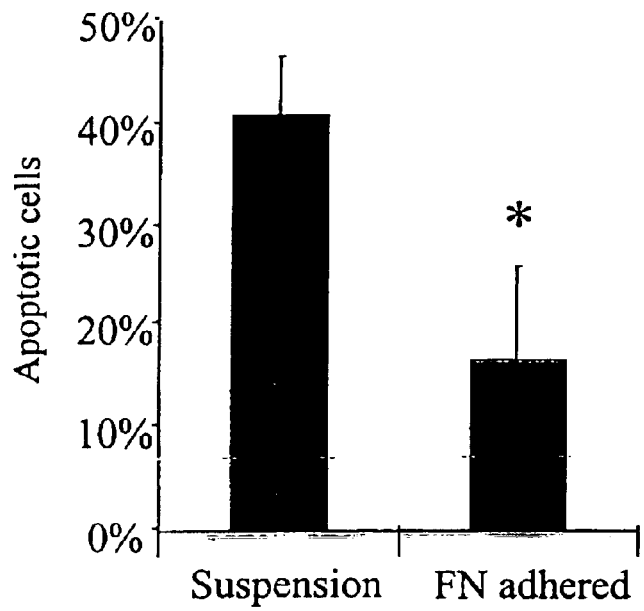
FIG. 2 illustrates Annexin V stained FN-adhered myeloma cells having a lower apoptotic fraction compared to non-adhered cells following acute drug exposure.
Figure 2:
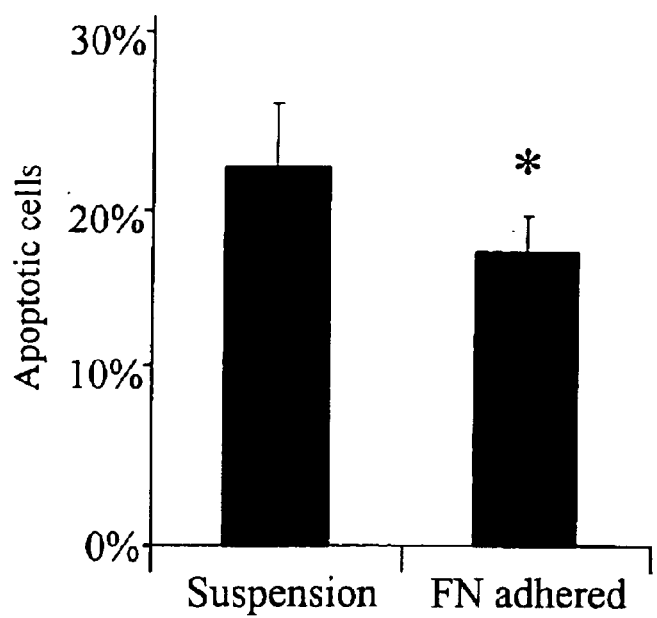

FIG. 2 illustrates Annexin V stained FN-adhered myeloma cells having a lower apoptotic fraction compared to non-adhered cells following acute drug exposure. 8226/S myeloma cells are exposed to 1 uM doxorubicin for one hour (a) or 50 uM melphalan for 24 hours (b), stained by Annexin V 24 hours later, then analyzed by flow cytometry. Histograms are adjusted for background staining in untreated cells, bars are the s.d. of three different experiments; *, P<0.05.

Figure 3:
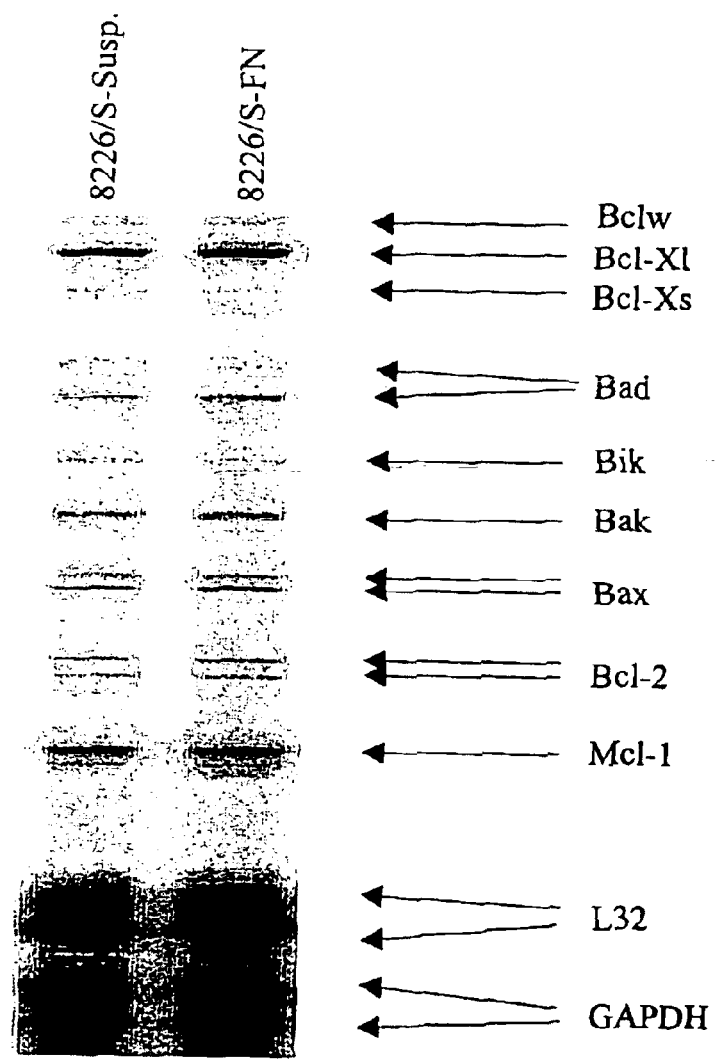
FIG. 3 illustrates the fact that RNA levels of Bcl-2 family members are unchanged following FN adhesion.

FIG. 3 illustrates the fact that RNA levels of Bcl-2 family members are unchanged following FN adhesion. Drug sensitive-8226/S cells are adhered to FN-coated plates or grown in suspension for 24 hours after which total RNA is collected and analyzed by RNase protection. Expression levels are normalized to the housekeeping genes GAPDH and L32.

Figure 4:
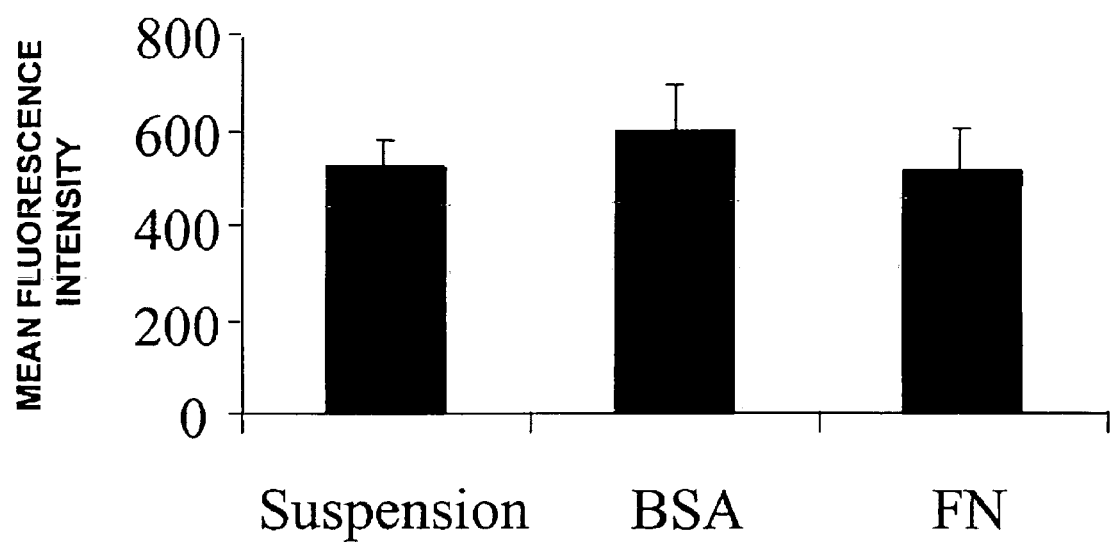
FIG. 4 illustrates the fact that intracellular doxorubicin concentration is to unaffected by culturing cells on plastic, or FN.

FIG. 4 illustrates the fact that intracellular doxorubicin concentration is unaffected by culturing cells on plastic, BSA, or FN. Following a 24 hour incubation on each surface, 10 uM doxorubicin is added to each well for one hour and cells are analyzed for drug accumulation differences by flow cytometry. Bars are the s.d. of n=6 from two independent experiments.

Figure 5:
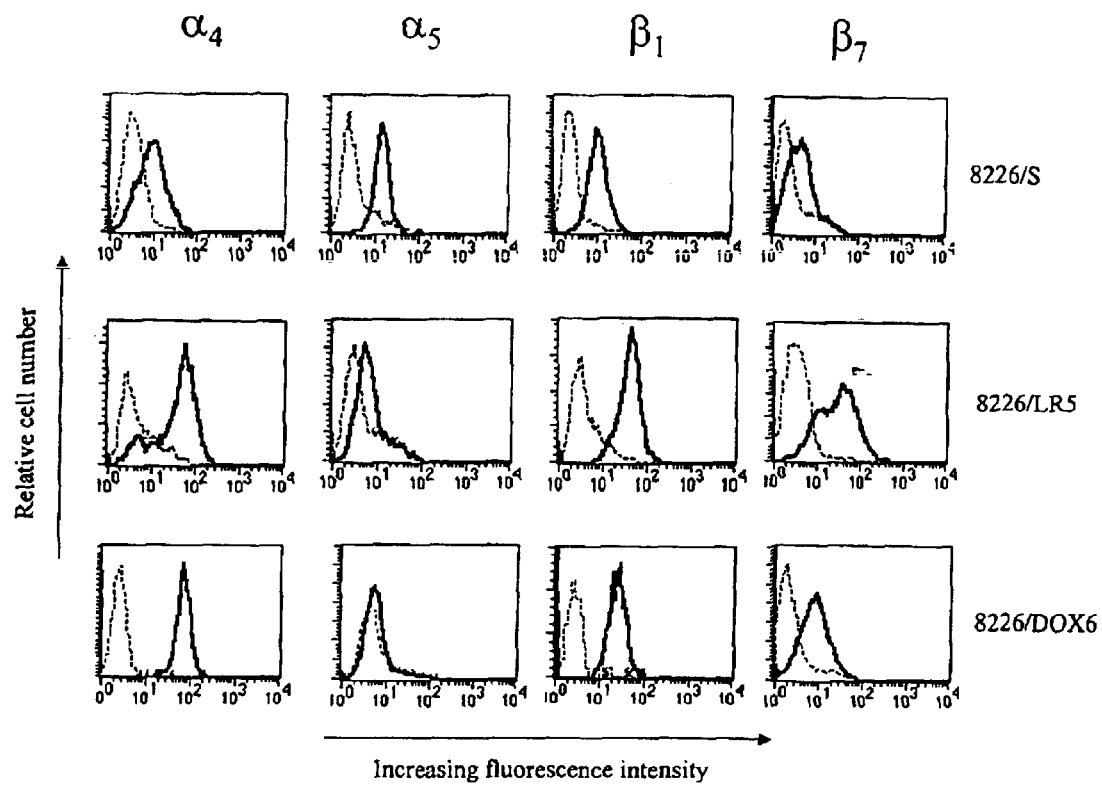
FIG. 5 illustrates phenotypic analysis of 8226 cell surface FN receptor expression by flow cytometry.

FIG. 5 illustrates phenotypic analysis of 8226 cell surface FN receptor expression by flow cytometry. Integrin subunit expression by drug sensitive (8226/S), melphalan resistant (8226/LR5), and doxorubicin resistant (8226/DOX6) cell lines are analyzed using monoclonal antibodies for $\alpha_4$, $\alpha_5$, $\beta_1$ and $\beta_7$. Cells are incubated with an integrin-specific mAb (—) or with irrelevent control Ab (---), followed by incubation with FITC-conjugated secondary Ab. 10,000 events are analyzed for each sample using a FACScan machine (Becton-Dickinson), histograms are representative of three different experiments.

Figure 6A:
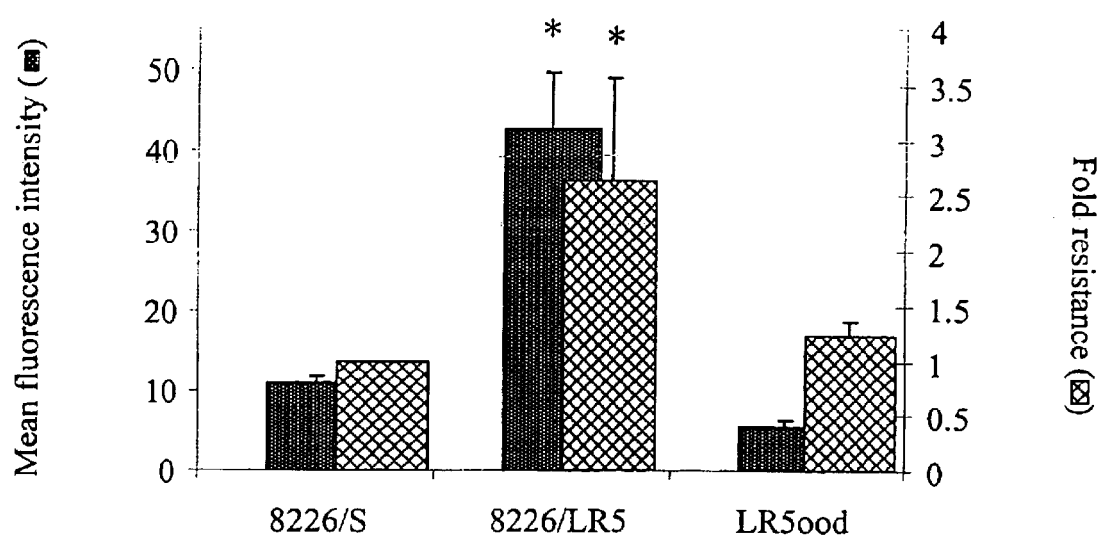
FIG. 6A illustrates drug resistance associated with $\alpha_4$ expression in melphalan resistant (8226/LR5) and revertant (LR5ood) cell lines

FIG. 6A illustrates drug resistance associated with $\alpha_4$ expression in melphalan resistant (8226/LR5) and revertant (LR5ood) cell lines. 8226/LR5 are maintained in $5 \times 10^{-5}$ M melphalan (LPAM) and LR5ood are maintained out of drug for 20 weeks. $\alpha_4$ expression is measured by flow cytometry and drug resistance is measured by MTT cytotoxicity analysis. Resistance values are reported as the IC50 dose of LPAM relative to 8226/S. $\alpha_4$ expression levels and melphalan resistance levels of 8226/LR5 are found to be higher than 8226/S (P<0.05). $\alpha_4$ expression and melphalan resistance of LR5ood are found to be equal to those of the 8226/S parent line. Bars are the s.d. of three different experiments.

Figure 6B:
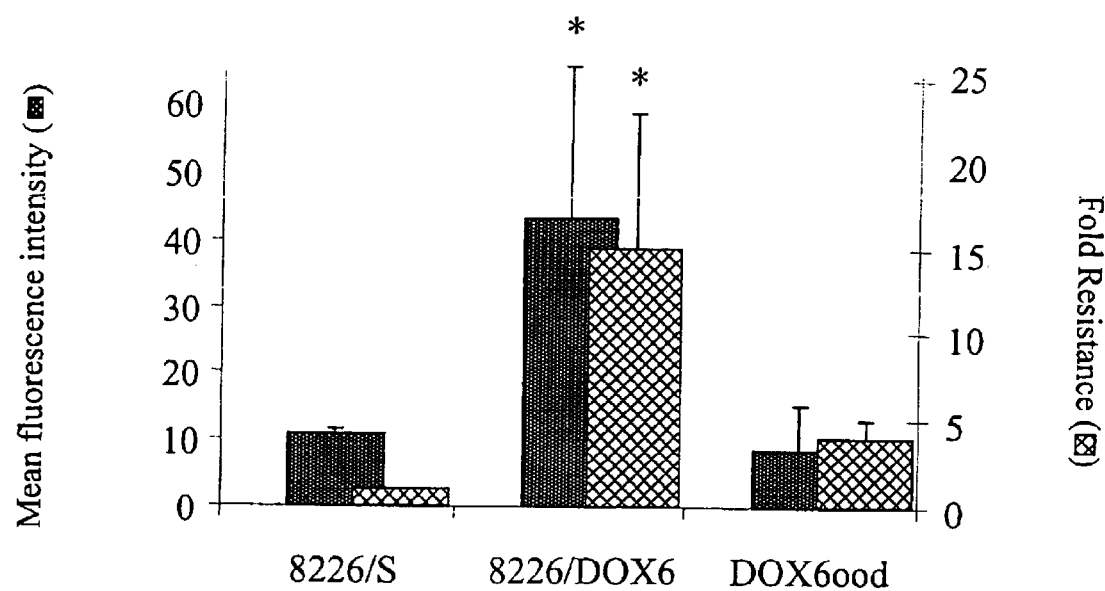
FIG. 6B illustrates drug resistance associated with $\alpha_4$ expression in doxorubicin resistant (8226/DOX6) and revertant (DOX6ood) cell lines.

FIG. 6B illustrates drug resistance associated with $\alpha_4$ expression in doxorubicin resistant (8226/DOX6) and revertant (DOX6ood) cell lines. 8226/DOX6 are maintained $6 \times 10^{-8}$ M doxorubicin and DOX6ood are maintained out of drug for 20 weeks. $\alpha_4$ expression is measured by flow cytometry and drug resistance is measured by MTT cytotoxicity analysis. Resistance values are reported as the IC50 dose of doxorubicin relative to 8226/S. $\alpha_4$ expression levels and doxorubicin resistance levels of 8226/DOX6 are found to be higher than 8226/S (P<0.05). $\alpha_4$ expression and doxorubicin resistance of DOX6ood are found to be equal to those of the 8226/S parent line. Bars are the s.d. of three different experiments.

Figure 7:
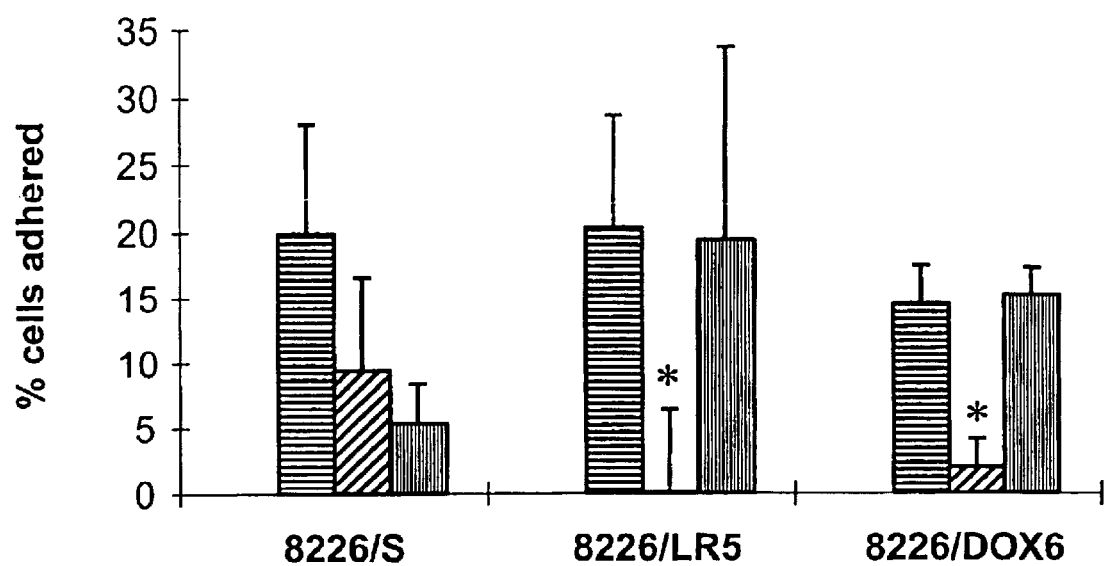
FIG. 7 illustrates the contribution of $\alpha_4$ and $\alpha_5$ integrin subunits to FN adhesion.

FIG. 7 illustrates the contribution of $\alpha_4$ and $\alpha_5$ integrin subunits to FN adhesion. Drug sensitive (8226/S), melphalan resistant (8226/LR5), and doxorubicin resistant (8226/DOX6) are adhered to FN-coated wells (horizontal striped bars) for one hour. To determine percentage binding due to $\alpha_4$ and $\alpha_5$, some cells are pre-incubated with $\alpha_4$ function blocking Ab P4G9 (hatched bars) or $\alpha_5$ function blocking Ab P1D6 (vertical striped bars) for 15 minutes prior to application to wells. FN adhesion by 8226/S is found to be mediated equally by $\alpha_4$ and $\alpha_5$ while FN adhesion for both drug resistant cell lines is mediated only by $\alpha_4$ (P<0.05), as determined by complete inhibition of adherence using the ($\alpha_4$ blocking Ab. Total FN adhesion mediated by $\alpha_4$ is also higher in drug resistant lines compared to drug sensitive 8226/S (P<0.05). Values shown are the % of total cells applied to each well corrected for non-specific adhesion to BSA-coated wells. Bars are the s.d. of n=6 from three different experiments.

Figure 8:
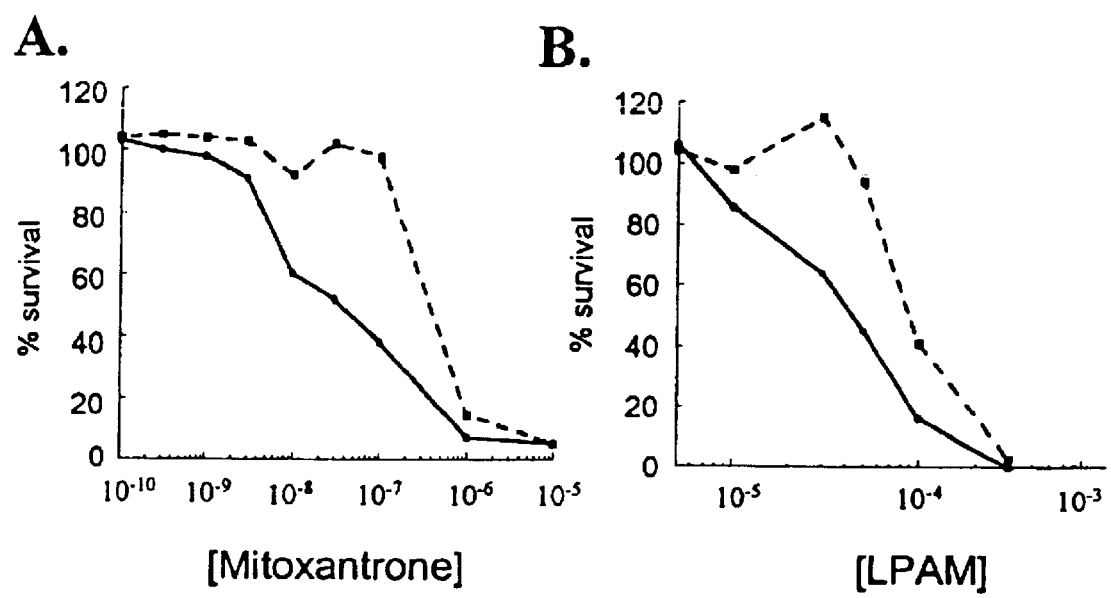
FIG. 8 illustrates K562 cells adhered to FN having a survival advantage over non-adhered cells following exposure to mitoxantrone and melphalan.

FIG. 8 illustrates K562 cells adhered to FN having a survival advantage over non-adhered cells following exposure to mitoxantrone and melphalan. Cell growth based MTT cytotoxicity assays are used to determine response to (A) mitoxantrone and (B) melphalan (LPAM). FN adhered cells (---) are bound to FN coated plates 24 hours prior to 96 hour drug exposure and control cells are grown in suspension (—). Data points are presented as cell viability determined by MTT dye reduction compared to untreated controls. Graphs are representative experiments that are repeated 3 times in replicates of 4.

Figure 9:
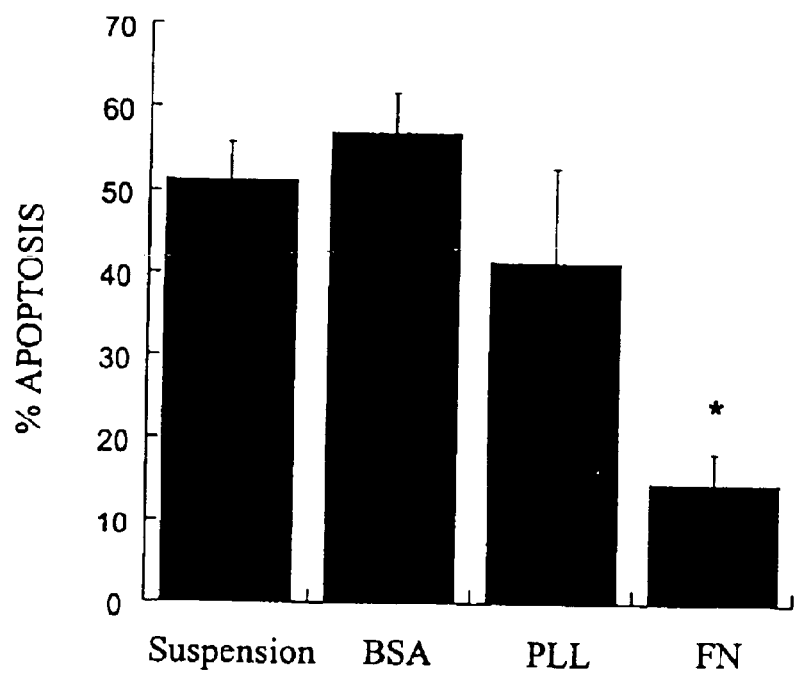
FIG. 9 illustrates the fact that K562 cells are resistant to melphalan-induced apoptosis only following FN-specific adhesion.

FIG. 9 illustrates the fact that K562 cells are resistant to melphalan-induced apoptosis only following FN-specific adhesion. Cells are seeded on each matrix for two hours, exposed to 100 $\mu$M LPAM for 90 minutes, washed, and incubated for 24 hours. Percent apoptosis is determined by Annexin V staining and flow cytometry, during which 5000 events are analyzed for each sample. Bars represent standard deviations and * denotes significant reduction in apoptosis by Student's t-test (p<0.05).

Figure 10:
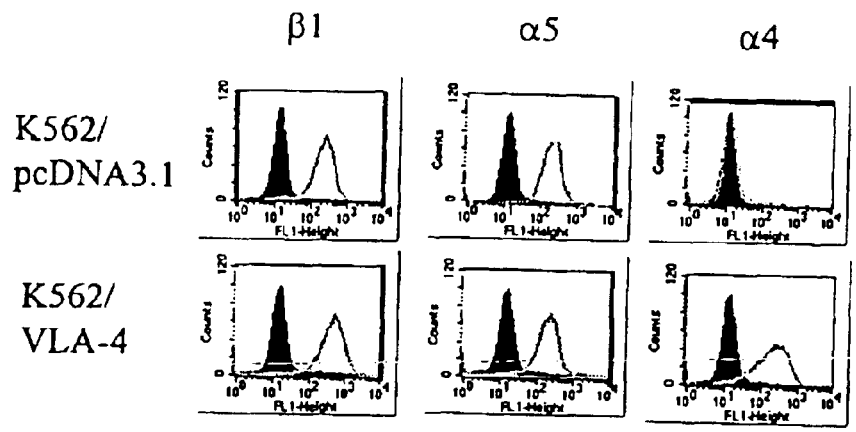
FIG. 10 illustrates the fact that K562/VLA-4 overexpresses the α4 integrin subunit.
Figure 10:
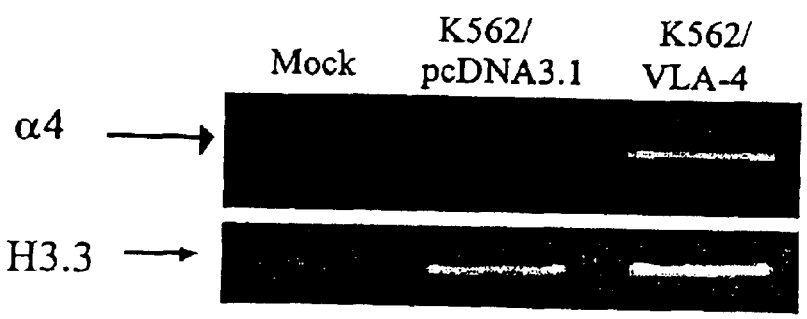

FIG. 10 illustrates the fact that K562/VLA-4 overexpresses the $\alpha4$ integrin subunit. K562/VLA-4, but not K562/pcDNA3.1, expresses the $\alpha4$ subunit protein on its surface, as determined by flow cytometry (A). $\alpha4$ mRNA is only present in K562/VLA-4 by RT-PCR analysis (B).

Figure 11:
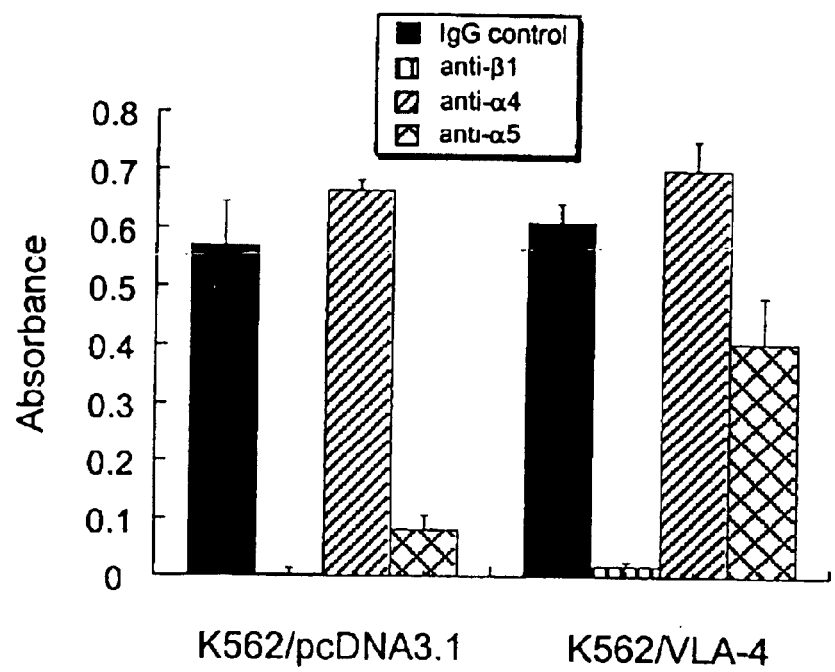
FIG. 11 illustrates the fact that K562/pcDNA3.1 adheres to FN via VLA-5 while K562/VLA-4 adheres to FN via VLA-4 and VLA-5.

FIG. 11 illustrates the fact that K562/pcDNA3.1 adheres to FN via VLA-5 while K562/VLA-4 adheres to FN via VLA-4 and VLA-5. Cell adhesion is determined using integrin blocking antibodies and a calorimetric assay. Cells are pretreated with $\beta$1 activating mAb B3B11 (1:100) and blocking mAb prior to application to FN coated wells for one hour. Absorbance values shown are the mean of three replicates, with background binding to BSA subtracted from each. Experiments are repeated 3 times.

Figure 12:
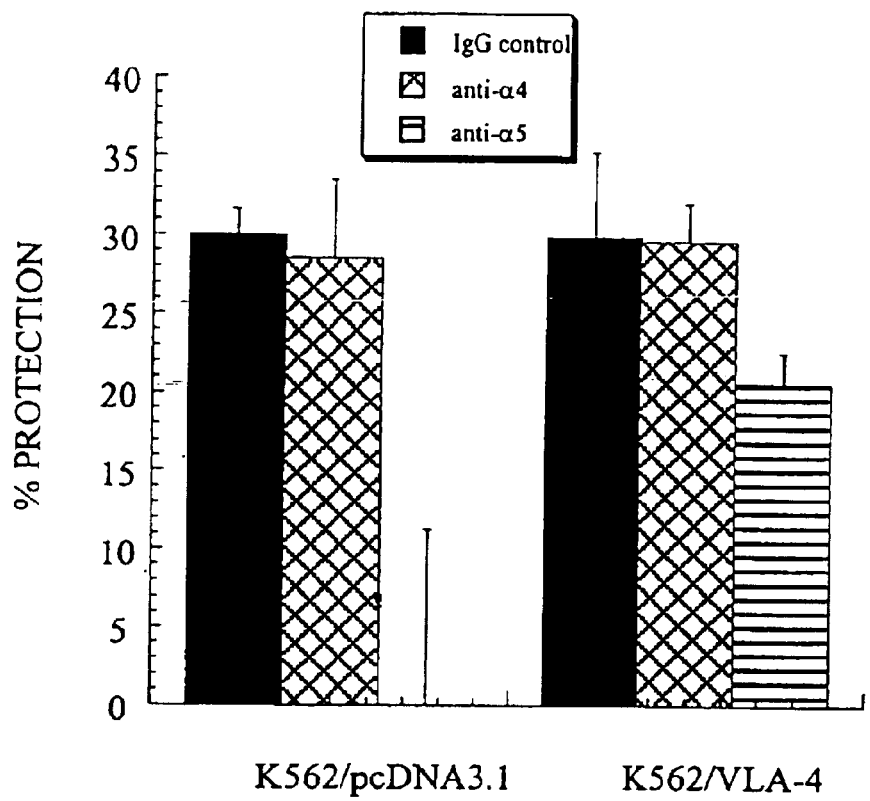
FIG. 12 illustrates the fact that α4 and α5-mediated FN adhesion induce cell adhesion mediated drug resistance but the effects of each receptor are not additive.

FIG. 12 illustrates the fact that $\alpha4$ and $\alpha5$-mediated FN adhesion induce cell adhesion mediated drug resistance but the effects of each receptor are not additive. Cells are pretreated with mAb B3B11, then with anti-$\alpha4$ blocking mAb (P4G9), anti-$\alpha5$ blocking mAb (P1D6), or IgG3 isotype control Ab prior to adhesion to FN coated dishes. Cells are exposed to 100 $\mu$M LPAM for 90 minutes, washed, incubated for 24 hours, and analyzed using Annexin V staining and flow cytometry. Bars are the standard deviations of three independent experiments performed in duplicate, * denotes p<0.05 by Student's t-test.

Figure 13:
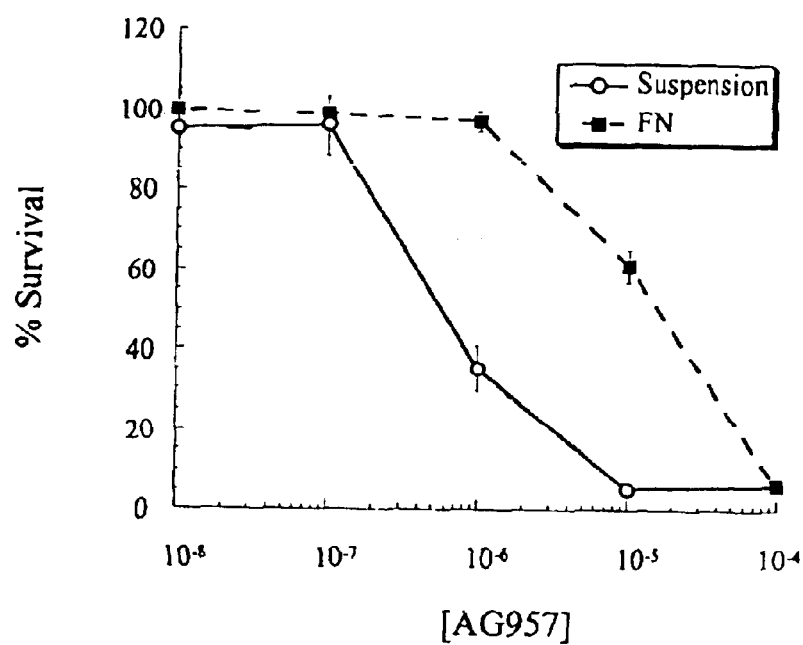
FIG. 13 illustrates the fact that K562 cells adhered to FN are resistant to the cytotoxic effects of the BCR/ABL inhibitor AG957.

FIG. 13 illustrates the fact that K562 cells adhered to FN are resistant to the cytotoxic effects of the BCR/ABL inhibitor AG957. The MTT assay is used to evaluate sensitivity of suspension grown and FN adhered K562 cells treated with AG957 for 96 hours. The mean IC50 for suspension grown cells (—) is $3.60 \times 10^{-6}$M compared to $12.95 \times 10^{-6}$M for FN adhered cells (---). Graph shown is representative of three independent experiments which are significantly different at p<0.05 by Student's t-test.

Figure 14:
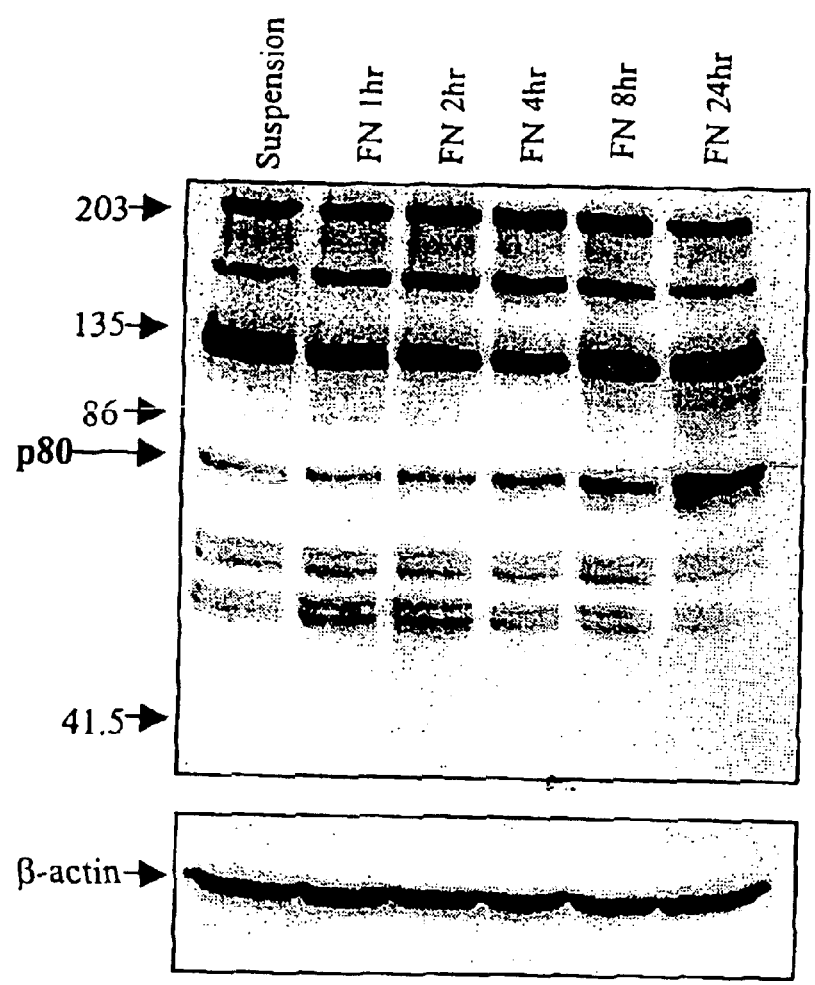
FIG. 14 illustrates the fact that phosphorylation of an 80 kDa protein is detectable FN adhered K562 cells.

FIG. 14 illustrates the fact that phosphorylation of an 80 kDa protein is detectable FN adhered K562 cells. Cells are adhered to FN for the times indicated or are kept in suspension, then analyzed for the presence of phosphorylated tyrosine residues. Western blotting using anti-phosphotyrosine mAb is used to determine activity and $\beta$-actin is used as a control for equal protein loading.

Figure 15:
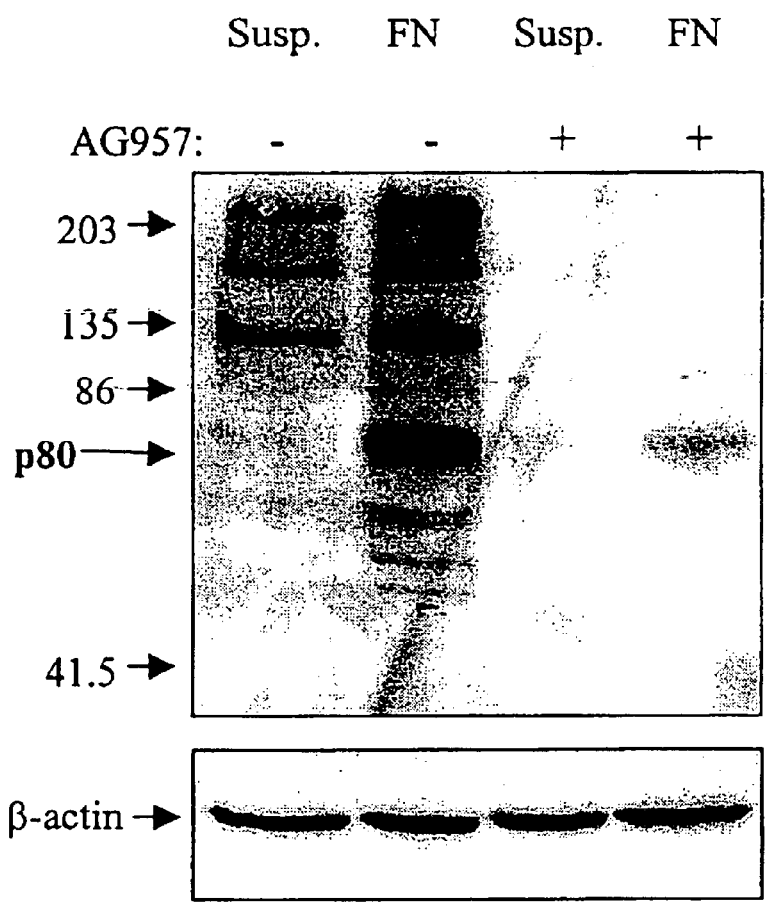
FIG. 15 illustrates the fact that integrin activation does not reconstitute BCR/ABL-associated tyrosine kinase activity in AG957 treated cells.

FIG. 15 illustrates the fact that integrin activation does not reconstitute BCR/ABL-associated tyrosine kinase activity in AG957 treated cells. K562 cells are adhered to FN or kept in suspension for 24 hours, after which they are exposed to 20 $\mu$M AG957 or DMSO (vehicle control) for four hours. Proteins are separated by 10% SDS-PAGE and subjected to anti-phosphotyrosine immunoblotting. AG957 abrogates all phosphotyrosine activity with the exception of the 80 kda protein, which persists to a small degree. Blot shown is representative of three independent experiments.

Figure 16:
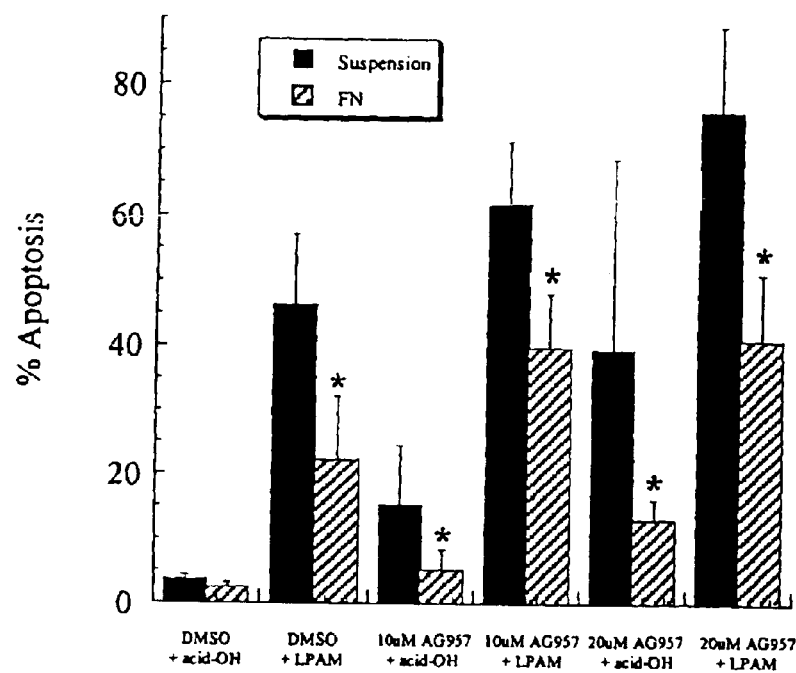
FIG. 16 illustrates FN adhered cells maintaining the CAM-DR phenotype during AG957 exposure.

FIG. 16 illustrates FN adhered cells maintaining the CAM-DR phenotype during AG957 exposure. K562 cells are adhered to FN (striped bars) or kept in suspension (solid bars) for three hours, treated with AG957 (or DMSO vehicle control) for two hours, then exposed to 100 $\mu$M LPAM (or Acid-OH vehicle control) for 90 minutes. Apoptosis is analyzed 24 hours later by Annexin V staining and flow cytometry. Graph is representative of three independent experiments performed in duplicate. * indicates % apoptosis (FN vs. suspension) is significantly different (p<0.05 by Student's t-test).

Figure 17:
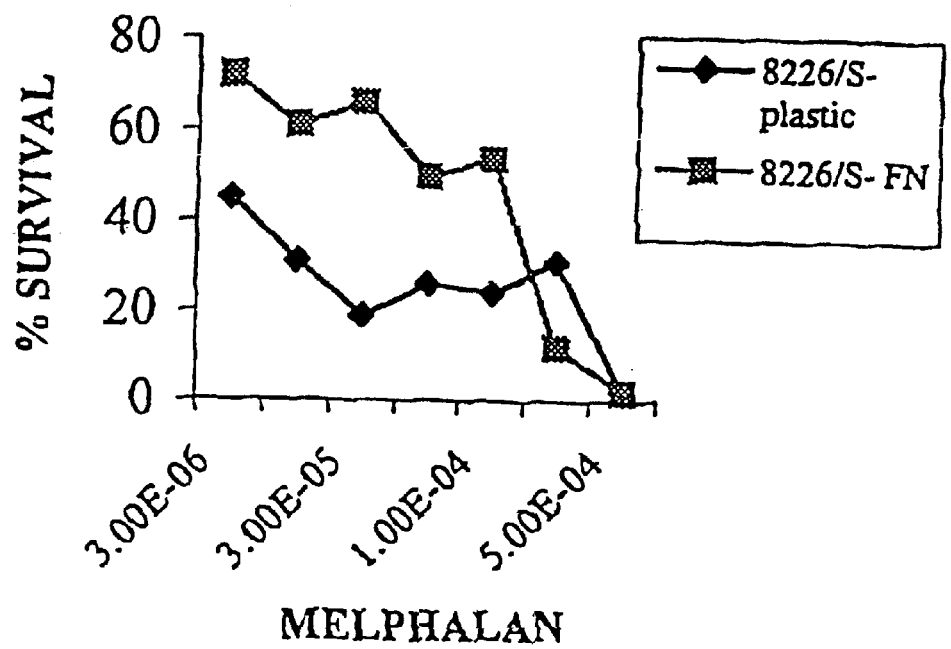
FIG. 17 illustrates resistance to cytotoxic drugs resulting from adhesion of myeloma cells to fibronectin.

FIG. 17 illustrates resistance to cytotoxic drugs resulting from adhesion of myeloma cells to fibronectin. Adhesion of myeloma cells to FN results in resistance to cytotoxic drugs. 8226 myeloma cells grown on FN-coated plates are less sensitive to the cytotoxic effects of doxorubicin and melphalan as determined by MTT cell viability assays and Annexin V analysis.

Figure 18:
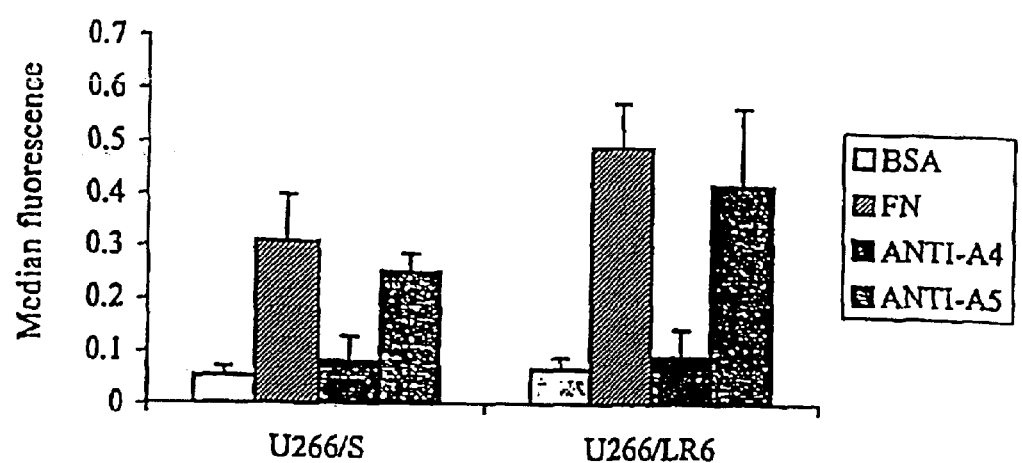
FIG. 18 illustrates upregulation of expression of VLA-4 and increased adhesion to fibronectin due to selection for drug resistance to melphalan and doxorubicin in myeloma cell lines.

FIG. 18 illustrates upregulation of expression of VLA-4 and increased adhesion to fibronectin due to selection for drug resistance to melphalan and doxorubicin in myeloma cell lines. Selection for drug resistance to melphalan and doxorubicin in myeloma cell lines results in upregulation of expression of VLA-4 and increased adhesion to FN. Human myeloma cell lines 8226 and U266 adhere to fibronectin (FN) through $\beta$1 integrin interactions (VLA-4 and VLA-5). Melphalan and doxorubicin resistant variants of these cell lines show increased levels of VLA-4 mediated adhesion to FN as determined by anti-integrin mAbs.

Figure 19:
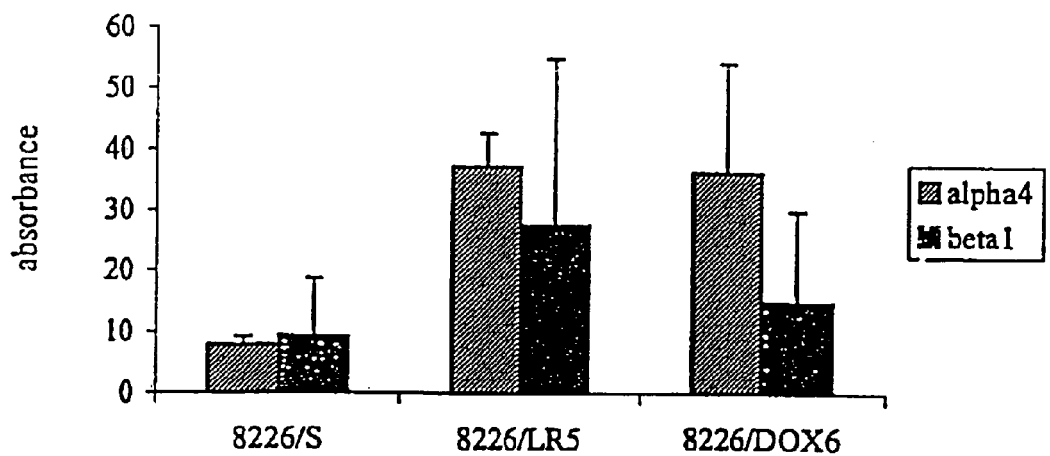
FIG. 19 illustrates overexpression of VLA-4 by melphalan resistant and doxorubin resistant cell lines.

FIG. 19 illustrates overexpression of VLA-4 by melphalan resistant and doxorubin resistant cell lines. Melphalan resistant (8226/LR5) and doxor-ubicin resistant (8226/Dox6) cell lines overexpress VLA-4 (a4p I integin heterodimer), as determined by FACS analysis.

Figure 20:
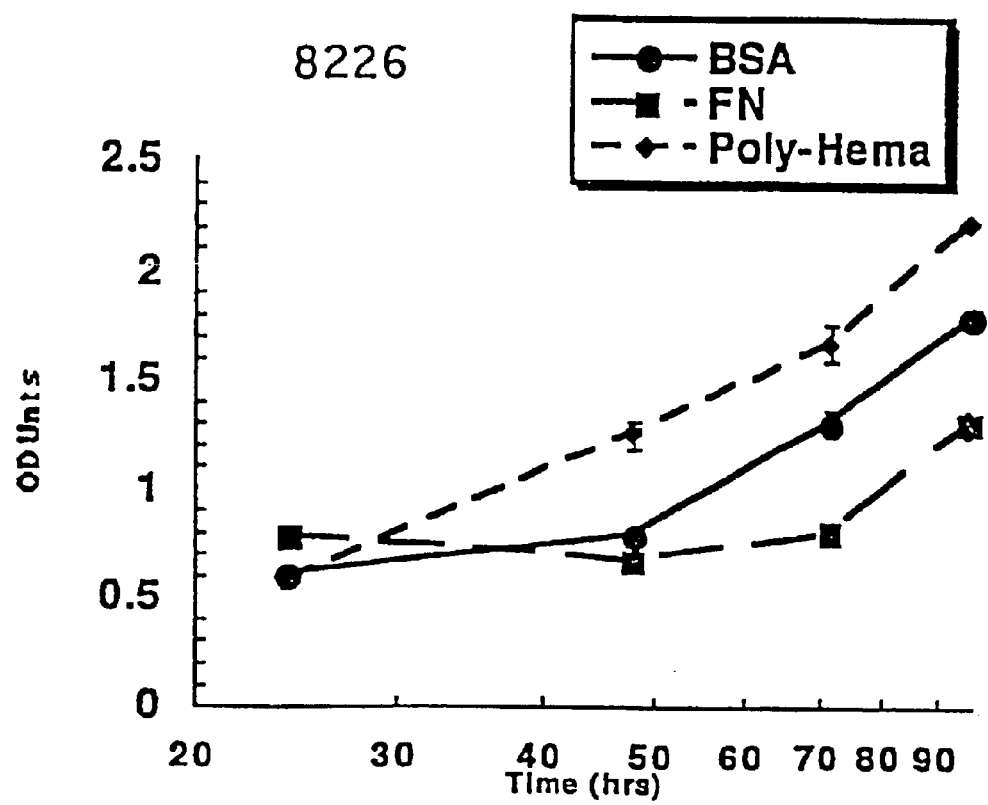
FIG. 20 illustrates the fact that myeloma cells that express VLA-4 and VLA-5 undergo G1 arrest when adhered to fibronectin.

FIG. 20 illustrates the fact that myeloma cells that express VLA-4 and VLA-5 undergo G1 arrest when adhered to fibronectin. 96 well plates are coated with 50 $\mu$g/ml fibronectin (FN), 0.01 percent BSA or two percent Poly-Hema (prevents adhesion to plastic) per well. Cells are allowed to adhere for one hour to fibronectin in serum free media, unadhered cells are then washed and 200 $\mu$l RPNH media containing 5 percent FBS is added back to each well. Growth is measured by MTT at 24, 48, 72 and 96 hours.

Figure 21:
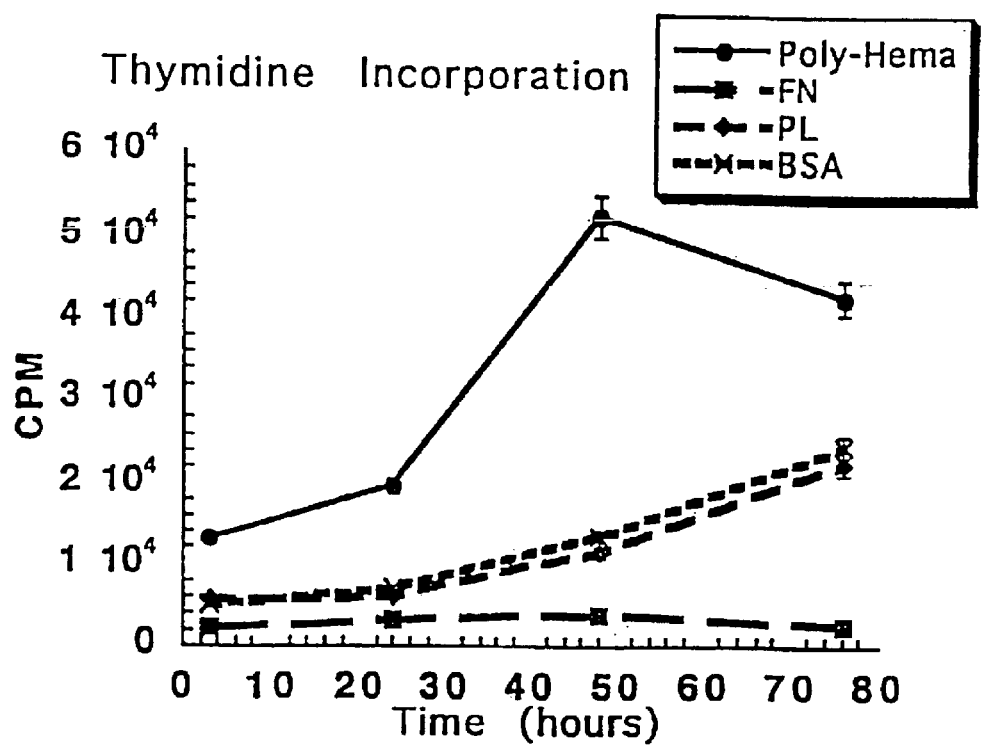
FIG. 21 illustrates thymidine incorporation.

FIG. 21 illustrates thymidine incorporation. 96 well plates are coated with 50 $\mu$g/ml fibronectin (FN), 0.01 percent BSA or two percent Poly-Hema (prevents adhesion to plastic) per well. Cells are allowed to adhere for one hour to fibronectin in serum free media and, unadhered cells are removed and 200 $\mu$l RPMI media containing 5 percent FBS is added back to each well. Cells are pulsed with two $\mu$Ci 3H-thymidine for three hours at each respective time point. A cell harvester is used to collect DNA, and labeled DNA is counted on a scintillation counter.

Figure 22:
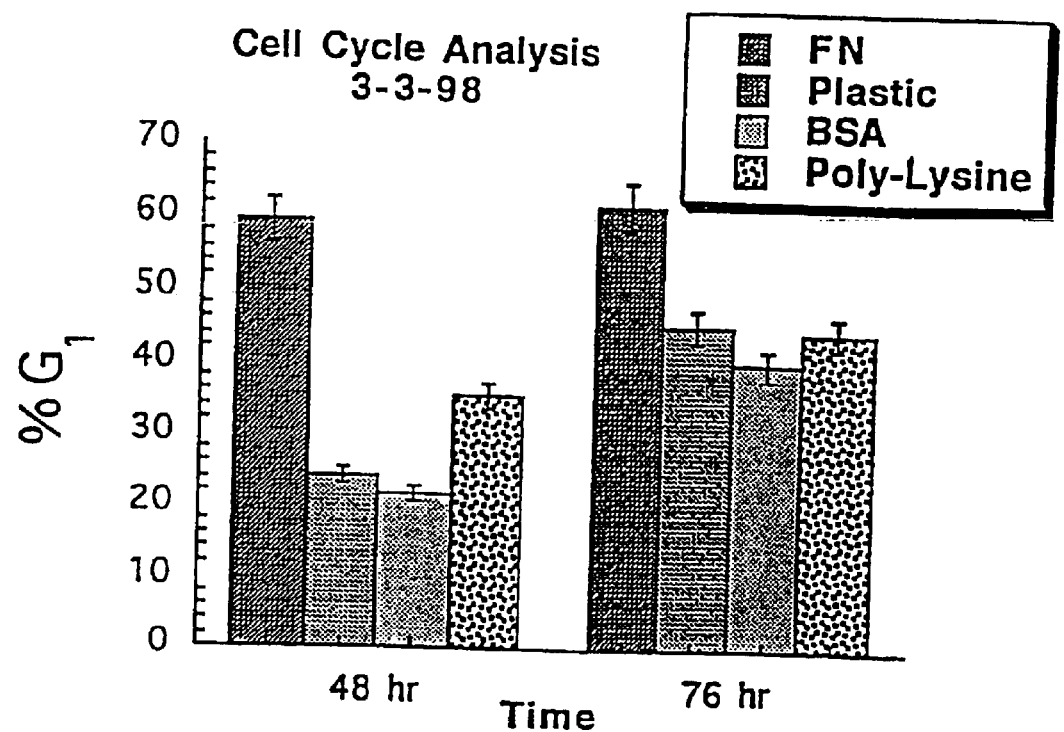
FIG. 22 illustrates the percentage of cells in G1.

FIG. 22 illustrates the percentage of cells in G1. Cells are allowed to adhere to fibronectin or poly-lysine coated plates for 48 or 76 hours. Unattached cells are removed by washing the plate with PBS before removing adhered cells. Cells which adhere to fibronectin are removed with PBS containing two mM EDTA. Cells are fixed, RNA is digested with RNase and the nuclei are stained with propidium iodide. Cell cycle is analyzed by FACS and a Cell Lysis software program is used to determine the percentage of cells in G1.

Figure 23:
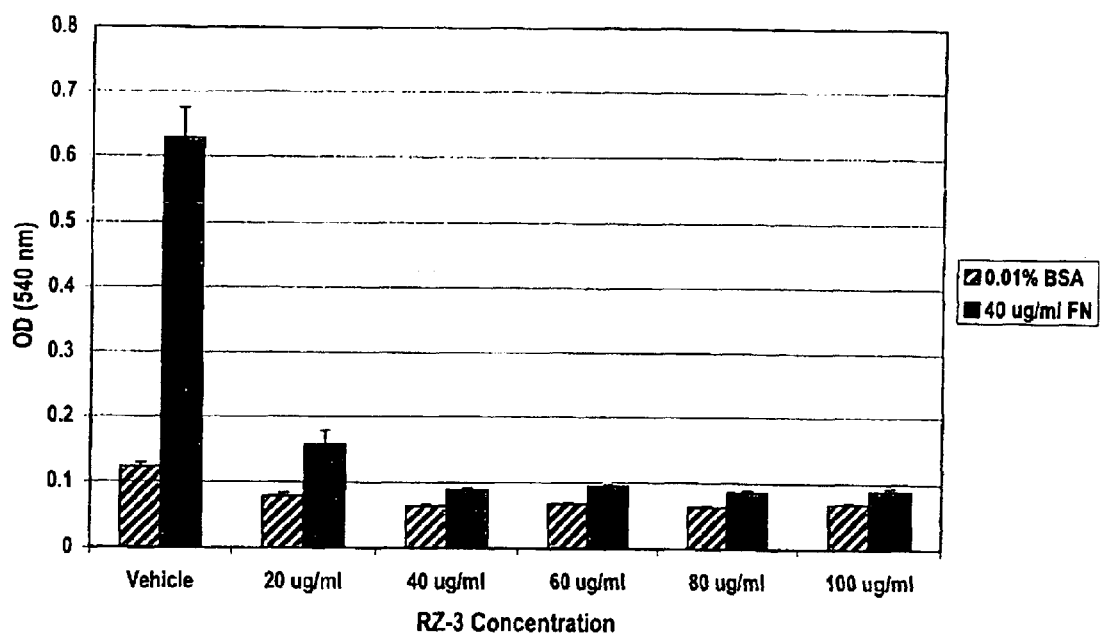
FIG. 23 illustrates the effect of the D-amino acid peptide RZ-3 on adhesion of 8226 cells.

Overexpression of CDK inhibitors correlates with a decrease in sensitivity to chemotheurapeutic agents. Cells that have been arrested in G1 have an increased capacity to repair DNA damage induced by DNA damaging agents such as cis-platinum and doxorubicin. Thus, physiological mediators of G1 arrest are important targets for sensitizing cells to existing chemotheurapeutic agents FIG. 23 illustrates the effect of the D-amino acid peptide RZ-3 on adhesion of 8226 cells. 8226 myeloma cells are treated with varying concentrations of RZ-3, (ranging from 20 µg/ml to 100 µg/ml) followed by plating on to BSA or fibronectin (FN) coated plates. Cells do not adhere significantly to BSA but do significantly adhere to FN. RZ-3 is effective in preventing FN adhesion.

Figure 24:
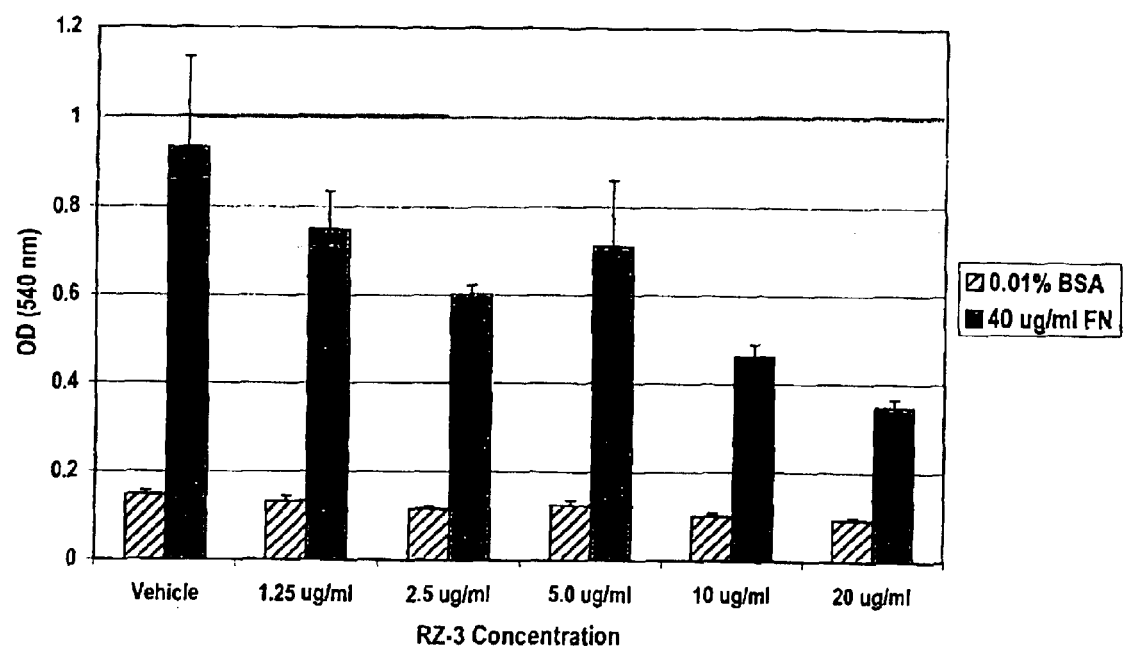
FIG. 24 illustrates the effect of the D-amino acid peptide RZ-3 on adhesion of 8226 cells.

FIG. 24 illustrates the effect of the D-amino acid peptide RZ-3 on adhesion of 8226 cells. 8226 myeloma cells are treated with varying concentrations of RZ-3, (ranging from 1.25 µg/ml to 20 µg/ml) followed by plating on to BSA or fibronectin (FN) coated plates. Cells do not adhere significantly to BSA but do significantly adhere to FN. RZ-3 is effective in preventing FN adhesion.

Figure 25:
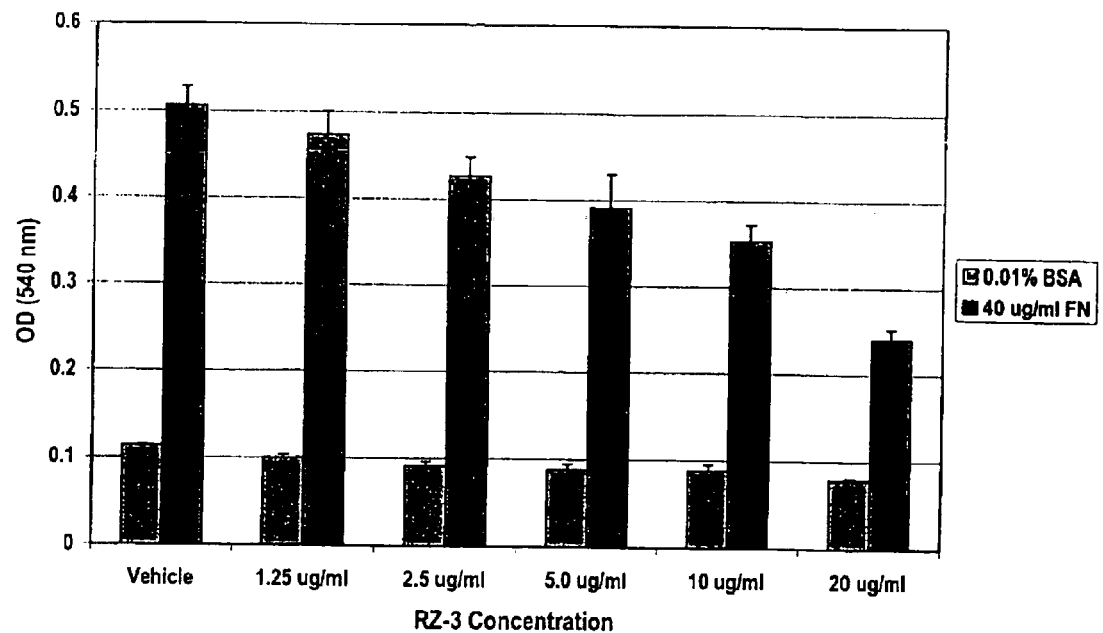
FIG. 25 illustrates the effect of (he D-amino acid peptide RZ-3 on adhesion of 8226 cells.

FIG. 25 illustrates the effect of the D-amino acid peptide RZ-3 on adhesion of 8226 cells. 8226 myeloma cells are treated with varying concentrations of RZ-3, (ranging from 1.25 µg/ml to 20 µg/ml) followed by plating on to BSA or fibronectin (FN) coated plates. Cells do not adhere significantly to BSA but do significantly adhere to FN. RZ-3 is effective in preventing FN adhesion.

Figure 26:
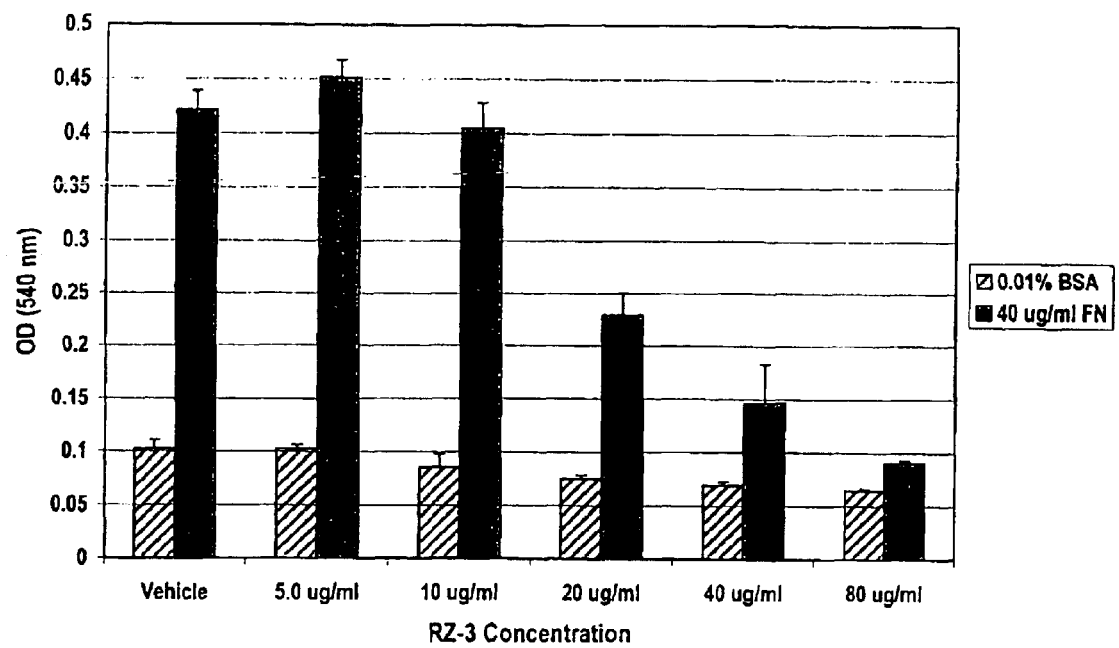
FIG. 26 illustrates the effect of the D-amino acid peptide RZ-3 on adhesion of U937 cells.

FIG. 26 illustrates the effect of the D-amino acid peptide RZ-3 on adhesion of U937 cells. U937 cells are treated with varying concentrations of RZ-3, (ranging from 5 µg/ml to 80 µg/ml) followed by plating on to BSA or fibronectin (FN) coated plates. Cells do not adhere significantly to BSA but do significantly adhere to FN. RZ-3 is effective in preventing FN adhesion.

Figure 27:
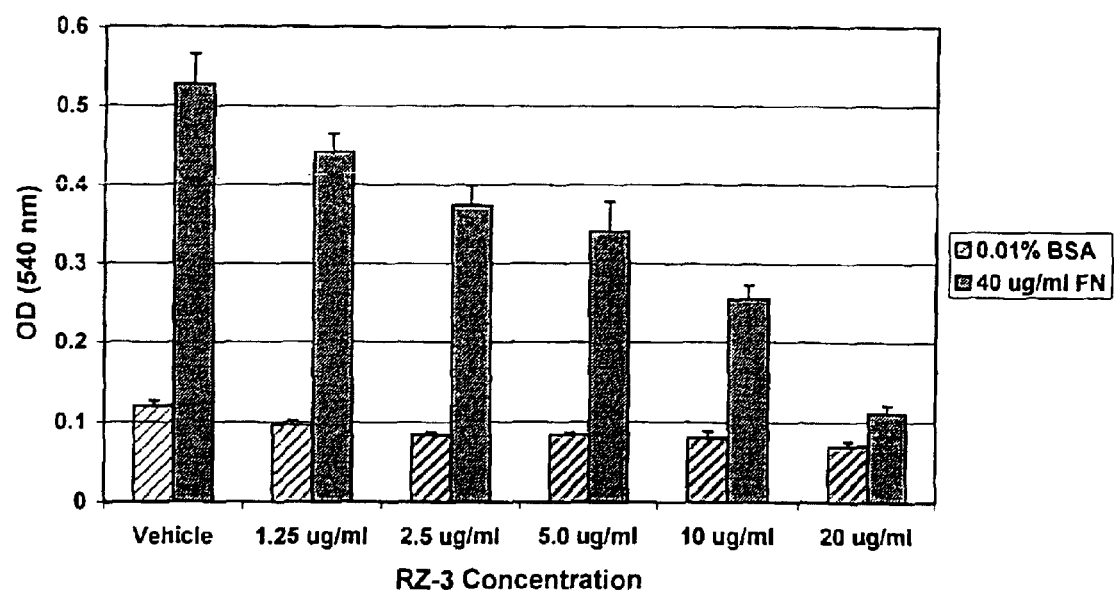
FIG. 27 illustrates the effect of the D-amino acid peptide RZ-3 on adhesion of 8226 cells, wherein the cells are treated with RZ-3 for thirty minutes and then adhered for two hours.

FIG. 27 illustrates the effect of the D-amino acid peptide RZ-3 on adhesion of U937 cells. 8226 myeloma cells are treated with varying concentrations of RZ-3, (ranging from 1.25 µg/ml to 20 µg/ml) for 30 minutes, followed by plating on to BSA or fibronectin (FN) coated plates. Cells do not adhere significantly to BSA but do significantly adhere to FN. RZ-3 is effective in preventing FN adhesion.

Figure 28:
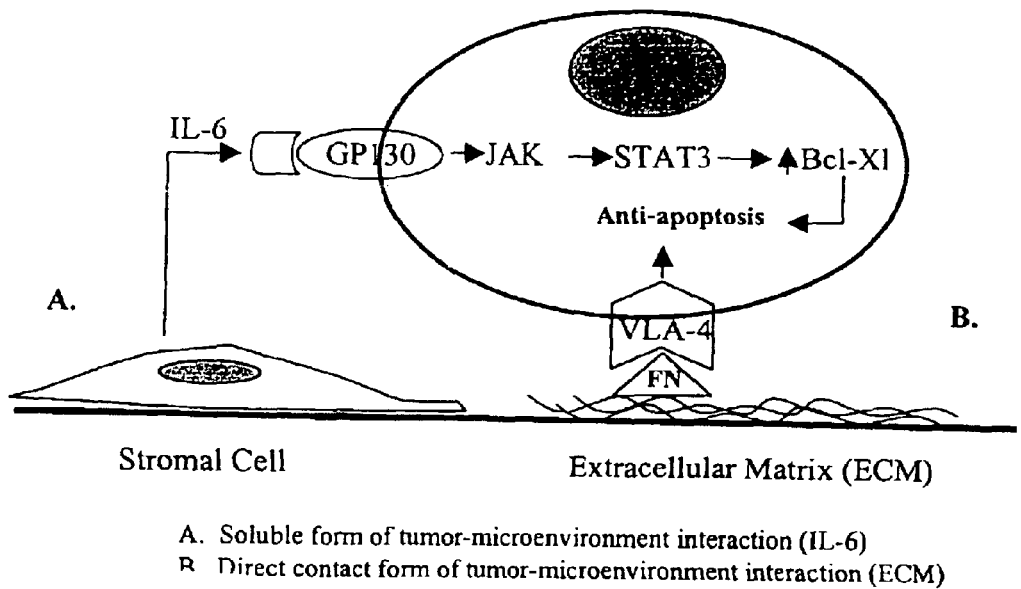
FIG. 28 illustrates two different forms of tumor-microenvironment interactions influencing drug response in cancer.

FIG. 28 illustrates the soluble form of tumor-microenvironment interaction (IL-6) as well as the direct contact form of tumor-microenvironment interaction (ECM).

BRIEF DESCRIPTION OF THE SEQUENCES

SEQ ID NO:1 is an upstream primer.
SEQ ID NO:2 is a downstream primer.
SEQ ID NO:3 is an upstream primer.
SEQ ID NO:4 is a downstream primer.
SEQ ID NO:5 is the amino acid sequence Lys-Met-Val-Ile-Tyr-Trp-Lys-Ala-Gly.
SEQ ID NO:6 is the RZ-3 peptide, the amino acid sequence Lys-Met-Val-Ile-Tyr-Trp-Lys-Ala-Gly, wherein each amino acid is a D-amino acid.

DETAILED DESCRIPTION OF THE INVENTION

Peptides as described herein may comprise residues of L-amino acids, D-amino acids, or any combination thereof. Amino acids may be from natural or non-natural sources, provided that at least one amino group and at least one carboxyl group are present in the molecule. The 20 L-amino acids commonly found in proteins are identified herein by the conventional one-letter abbreviations known in the art, and the corresponding D-amino acids are designated by a lower case one letter symbol. Peptides may also contain one or more rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylamino), with or without any of a wide variety of side chain modifications and/or substitutions (e.g., methylation, benzylation, t-butylation, tosylation, alkoxycarbonylamino, and the liked). Such modifications and derivatives of a peptide sequence, and others known to those of skill in the art, are herein termed "variants." Preferred derivatives include amino acids having an N-acetyl group (such that the amino group that represents the N-terminus of the linear peptide is acetylated) and/or a C-terminal amide group (i.e., the carboxy terminus of the linear peptide is amidated). Residues other than common amino acids that may be present include, but are not limited to, penicillamine, tetramethylene cysteine, pentamethylene cysteine, mercaptopropionic acid, pentamethylene-mercaptopropionic acid, 2-mercaptobenzene, 2-mercaptoaniline, 2-mercaptoproline, ornithine, diaminobutyric acid, aminoadipic acid, m-aminomethylbenzoic acid and diaminopropionic acid.

Peptides as described herein may be synthesized by methods well known in the art, including recombinant DNA methods and chemical synthesis. Chemical synthesis may generally be performed using standard solution phase or solid phase peptide synthesis techniques, in which a peptide linkage occurs through the direct condensation of the amino group of one amino acid with the carboxy group of the other amino acid with the elimination of a water molecule. Peptide bond synthesis by direct condensation, as formulated above, requires suppression of the reactive character of the amino group of the first and of the carboxyl group of the second amino acid. The masking substituents must permit their ready removal, without inducing breakdown of the labile peptide molecule.

In solution phase synthesis, a wide variety of coupling methods and protecting groups may be used (see Gross and Meienhofer, eds., "The Peptides: Analysis, Synthesis, Biology," Vol. 1–4 (Academic Press, 1979); Bodansky and Bodansky, "The Practice of Peptide Synthesis," 2d ed. (Springer Verlag, 1994)). In addition, intermediate purification and linear scale up are possible. Those of ordinary skill in the art will appreciate that solution synthesis requires consideration of main chain and side chain protecting groups and activation method. In addition, careful segment selection is necessary to minimize racemization during segment condensation. Solubility considerations are also a factor.

Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., J. Am. Chem. Soc. 85:2149, 1963, which involves assembling a linear peptide chain on a resin support using protected amino acids. Solid phase peptide synthesis typically utilizes either the Boc or Fmoc strategy, which are now well known in the art.

Those of ordinary skill in the art will recognize that, in solid phase synthesis, deprotection and coupling reactions must go to completion and the side-chain blocking groups must be stable throughout the entire synthesis. In addition, solid phase synthesis is generally most suitable when peptides are to be made on a small scale.

Acetylation of the N-terminal can be accomplished by reacting the final peptide with acetic anhydride before cleavage from the resin. C-amidation is accomplished using an appropriate resin such as methylbenzhydrylamine resin using the Boc technology.

The peptides disclosed here in may be modified by attachment of a second molecule that confers a beneficial property upon the peptide, such as increased half-life in the body, for example pegylation. Such modifications also fall within the scope of the term "variant" as used herein.

Covalent attachment of a molecule or solid support may generally be achieved by first reacting the support material with a bifunctional reagent that will also react with a functional group, such as a hydroxyl, thiol, carboxyl, ketone or amino group, on the modulating agent. A preferred method of generating a linkage is via amino groups using glutaraldehyde. A modulating agent may be linked to cellulose via ester linkages. Similarly, amide linkages may be suitable for linkage to other molecules such as keyhole limpet hemocyanin or other support materials.

Although peptides as described herein may preferentially bind to specific tissues or cells, and thus may be sufficient to target a desired site in vivo, it may be beneficial for certain applications to include an additional targeting agent. Accordingly, a targeting agent may also, or alternatively, be linked to a modulating agent to facilitate targeting to one or more specific tissues. As used herein, a "targeting agent," may be any substance (such as a compound or cell) that, when linked to a modulating agent enhances the transport of the modulating agent to a target tissue, thereby increasing the local concentration of the modulating agent. Targeting agents include antibodies or fragments thereof, receptors, ligands and other molecules that bind to cells of, or in the vicinity of, the target tissue. Known targeting agents include serum hormones, antibodies against cell surface antigens, lectins, adhesion molecules, tumor cell surface binding ligands, steroids, cholesterol, lymphokines, fibrinolytic enzymes and those drugs and proteins that bind to a desired target site.

For certain embodiments, it may be beneficial to also, or alternatively, link a drug to a modulating agent. As used herein, the term "drug" refers to any bioactive agent intended for administration to a mammal to prevent or treat a disease or other undesirable condition. Drugs include hormones, growth factors, proteins, peptides and other compounds. The use of certain specific drugs within the context of the present invention is discussed below.

Within certain aspects of the present invention, one or more modulating agents as described herein may be present within a pharmaceutical composition. A pharmaceutical composition comprises one or more modulating agents in combination with one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. A peptide may, but need not, be encapsulated within liposomes using well known technology. Compositions of the present invention may be formulated for any appropriate manner of administration, including for example, topical, oral, nasal, intravenous, intracranial, intraperitoneal, subcutaneous, or intramuscular administration. For certain topical applications, formulation as a cream or lotion, using well known components, is preferred.

Integrin-mediated adhesion influences cell survival and can prevent programmed cell death. Drug-sensitive 8226 human myeloma cells express both VLA-4 ($\alpha_4\beta_1$) and VLA-5 ($\alpha_5\beta_1$) integrin fibronectin (FN) receptors, and are relatively resistant to the apoptotic effects of doxorubicin and melphalan when pre-adhered to FN, as compared with cells grown in suspension. This cell adhesion mediated drug resistance, or CAM-DR, is not due to reduced drug accumulation or upregulation of anti-apoptotic Bcl-2 family members. As determined by flow cytometry, myeloma cell lines selected for drug resistance, with either doxorubicin or melphalan, overexpress VLA-4. Functional assays reveal a significant increase in $\alpha_4$-mediated cell adhesion in both drug-resistant variants compared with the drug-sensitive parent line. When removed from selection pressure, drug-resistant cell lines revert to a drug sensitive and $\alpha_4$-low phenotype.

It is therefore disclosed herein that FN-mediated adhesion confers a survival advantage for myeloma cells acutely exposed to cytotoxic drugs or radiotherapy by inhibiting drug-induced apoptosis. This finding explains how some cells survive initial drug exposure or radiotherapy and eventually express classical mechanisms of drug resistance such as MDR1 overexpression.

EXAMPLE ONE

Materials and Methods

Cell and culture condition

The RPMI 8226 human myeloma cell line (8226/S) is obtained from the American Type Culture Collection (Rockville, Md.). The drug resistant cell lines, 8226/DOX6 and 8226/LR5, are selected from 8226/S using step-wise increases of doxorubicin and melphalan, respectively, as described for example by Dalton W. et al., Characterization of a new drug-resistant human myeloma cell line that expresses P-glycoprotein, Cancer Res 46:2125, 1986 and Bellamy W T, et al., Development and characterization of a melphalan resistant human multiple myeloma cell line, Cancer Res 51:995, 1991. All cells are grown in suspension in RPMI 1640 medium supplemented with 5 percent fetal bovine-serum, 1 percent (vol/vol) penicillin (100 U/mL), streptomycin (100 U/mL), and 1 percent (vol/vol) L-glutamine (all from GIBCO-BRL, Grand Island, N.Y.). Cells are maintained at 37° C. in 5 percent $CO_2$-95 percent air atmosphere and subcultured every 6 days.

Drugs

Melphalan (L-phenylalanine nitrogen mustard, LPAM) is obtained from Sigma-Aldrich (St Louis, Mo.) and dissolved in acidified ethanol. Doxorubicin is obtained from Sigma Aldrich and dissolved in sterile $ddH_2O$.

Cytotoxicity assays

96-Well immunosorp plates (Nunc, Denmark) are coated with 50 µL (40 µg/mL) FN (GIBCO) or bovine serum albumin (BSA) overnight and one percent BSA is used to block nonspecific binding sites in the wells for one hour before the is experiment. Wells are washed with serum-free RPMI 1640 and aspirated. 8226/S cells are washed once and resuspended in serum-free RPMI 1640; then $4 \times 10^4$ cells per well (FN coated) or $8 \times 10^3$ cells per well (BSA coated) are added to each plate. Cells are incubated for one hour at 37° C. and five percent $CO_2$, washed with serum free media twice, and put back into serum-containing media. Following 24 hours in a tissue culture incubator, 20 µL of diluted drug or vehicle control is added to each well for one hour, after which media is removed and replaced by drug-free media. Following a 96-hour incubation, 50 µL MTT dye (Sigma) is added to each well for four hours. Plates are then centrifuged and each well aspirated. Dye is solubilized with 100 µL DMSO and plates are read at 540 nm on an automated microtiter plate reader. A blank well containing only media and drug is also run as a control in all experiments. $IC_{50}$ values are calculated by linear regression of percent survival versus drug concentration.

Annexin V apoptotic analysis

Cells, $1 \times 10^6$, are attached to FN-coated 6-well plates (Biosource, Camarillo, Calif.) for one hour in serum-free media and nonadhered cells are removed with two washes. Fresh media with serum is added to the plates, which are incubated for 24 hours; $1 \times 10^6$ cells are also added to uncoated 6-well plates (Boeringer-Mannheim, Indianapolis, Ind.). Cells are exposed to 1 µmol/L doxorubcin for one hour (plus a 24-hour drug-free incubation period) or 50 µmol/L LPAM for 24 hours. Cells are then collected with 5 mmol/L EDTA/PBS and washed. Phycoerythrin (PE)- or fluorescein isothiocyanate (FITC)-conjugated Annexin V (Clontech, Palo Alto, Calif.) is then added to $1 \times 10^5$ cells and 5,000 to 10,000 events are analyzed on a FACScan machine (Becton Dickinson).

RNA collection and cDNA synthesis from FN-adhered myeloma cells

Cells, $1 \times 10^6$, are attached to FN coated 6-well plates as previously described. Total cellular RNA is collected on 3 separate days using TRIzol reagent (GIBCO). RNA is quantitated on a spectophotometer at 260 nm and one µg is DNAse treated and requantitated. A single large scale cDNA reaction is prepared for each sample for use in PCR reactions. A 40 µL reverse transcription reaction containing 200 ng RNA, 1×PCR buffer (10 mmol/L Tris, pH 8.3–50 mmol/L MKCL-1.5 mmol/L $MgCl_2$), 1 mmol/L concentrations each of dATP, dGTP, dCTP, and dTTP; 200 pmol random hexamers, 40 U RNAse inhibitor, and 12 U avian megalovirus reverse transcriptase (Boeringer-Mannheim) is prepared on ice then incubated at 42° C. for one hour, 99° C. for 10 minutes, and quick chilled to 4° C.

RNase protection assay

Twenty micrograms of RNA is isolated from 8226/S cells grown in suspension or adhered to FN using TRIzol reagent and resuspended in hybridization buffer. Bcl-2 family specific probes are synthesized using a template set from Riboquant (San Diego, Calif.) and labeled using [$\alpha$-$^{32}$p]UTP and T7 polymerase. Probes are then column purified, quantitated on a scintillation counter, and $5 \times 10^5$ cmp is added to each sample. The hybridization reaction is carried out overnight at 56° C. Samples are then RNase treated for 45 minutes at 30° C., hybridized probes are extracted with chloroform: isoamyl alcohol and precipitated using 100 percent ethanol. Samples are then electrophoresed on a five percent polyacrylamide gel (7 mmol/L Urea), dried down, exposed to film, and analyzed by densitometry software (ImageQuaNT, Molecular Dynamics, Inc, Sunnyvale, Calif.). Unhybridized probes are used as size standards for each gene analyzed. Expression of Bcl-2, Bcl-Xl, Bcl-Xs, BAX, Bik, Bad, Bcl-w, Bak, Mcl-1, and Bfl I are quantitated by normalizing to GAPDH and L32 expression.

RT-PCR Analysis of BCL-2 Family Gene and Drug Transporter Expression

BCL-2 amplification is performed essentially as described by Tu Y et al., Upregulated expression of Bcl-2 in multiple myeloma cells induced by exposure to doxorubicin, etoposide, and hydrogen peroxide, Blood 88:1805,1996. Briefly, 20 µL of PCR reaction mixture (1×PCR buffer, 50 pmol of BCL-2 specific amp limers, 0.25 U Taq polymerase [Boehrin.-erMannheim], 1.25 µCi [$\alpha$-$^{32}$p]-dCTP) is added to 5 µL cDNA, followed by incubation at 94° C. for 5 minutes and then 26 cycles of 94° C. for one minute, 72° C. for one minute, and a final extension at 72° C. for five minutes in a thermal cycler (Perkin-Elmer Cetus). Histone 3.3 is amplified as described by Futscher Bwet al., Quantitative polymerase chain reaction analysis of MDR1 mRNA in multiple myetoma cell lines and clinical specimens, Anal Biochem 213:414, 1993, and is used as a control for RNA integrity and quantity. Bcl-XI and -Xs are amplified essentially as described by Benito A, et al., Apoptosis induced by erytheroid differentiation of human leukemia cell lines is inhibited by Bct-XL, Blood 87:3837, 1996, using 26 cycles of PCR. The 258 base pair BAX amplicon is amplified using the following primers (Biosynthesis, Lewisville, Tex.) and conditions: BAX-upstream (5'-ACCAAGAAGCTGA-GCGAGTGTC-TC-3') (SEQ ID NO:1), BAXdownstream (5'-CAATGTCCAGCCCATGATGG-3') (SEQ ID NO:2), cDNA denaturation for one minute at 94° C., annealing for 15 seconds at 60° C., primer extension for 15 seconds at 72° C., with a final extension for 5 minutes. All samples are loaded on a five percent nondenaturing polyacrylamide gel and electrophoresed for two hours at 80V. For determination of incorporated radionucleotide, gels are dried down and exposed to a phosphoroimaging plate (Molecular Dynamics, Inc) overnight. Plates are then scanned on a phosphorimager (Molecular Dynamics) and band intensities (pixels/unit area) for Bcl-2, Bcl-XI, Bcl-Xs, and BAX are analyzed normalized to Histone 3.3 expression. PCR amplification of the MDRI, MRP, and LRP genes is performed essentially as described by Abbaszadegan M. et al., Analysis of multidrug resistance-associated protein (MRP) messenger RNA in normal and malignant hematapoietic cells, Cancer Res 54:4676,1994, and Komarov P. et al., Activation of the LRP Oun-resistance-associated protein) gene by short-term exposure of human leukemia cells to phorbol ester and cytarabine, Oncology Res 10: 1 85, 1998, by using the housekeeping genes histone 3.3 (MDRI) or β-actin (MRP and LRP) as internal standards. cDNA synthesized from 8226/DOX6 RNA is used as a positive control for MDRI PCR. For all reactions, optimal cycle numbers are used and are within the exponential range of PCR amplification as determined by previous experiments.

Intracellular drug accumulation assay

Cells, $0.5 \times 10^6$, are adhered to FN-coated 6-well plates for 24 hours, as described previously. Control wells are coated with BSA or are uncoated. RPMI 1640 containing doxorubicin is added to each treatment well for a final concentration of 10 µmol/L. After one hour at 37° C., cells are washed three times with cold PBS and analyzed for FL-2 flourescence on a FACScan machine. Ten-thousand events are recorded for each condition, which are preformed in triplicate. Experiments are repeated twice.

Antibodies and phenotypic analysis of cell lines

Cell surface integrin expression is determined using the monoclonal antibodies (MoAbs) P4G9 (DAKO, Carpinteria, Calif.) for CDw49d ($\alpha_4$) analysis, A1A5 for CD29 ($\beta_1$) analysis (T Cell Diagnostics, Woburn, Mass., PID6 (DAKO) for CDw49e.($\alpha_5$) analysis, and FIB504 (Pharmingen, San Diego, Calif.) for $\beta_7$ analysis. Cells, $1 \times 10^6$, are incubated with primary antibody or an isotype control, then with FITC-conjugated goat anti-mouse or goat anti-rat secondary antibody. Fluorescence is then analyzed by flow cytometry with a FACScan machine, which records 10,000 events for each experiment.

Adhesion assays

Cells, $1.5 \times 10^5$, are adhered to FN- or BSA-coated well plates as described previously. After three washes to remove unattached cells, adherent cells are fixed in 70 percent methanol for 10 minutes. Following aspiration, wells are allowed to dry and then are stained with 0.02 percent crystal violet/0.2 percent ethanol for an additional 10 minutes. After solubilization with 100 $\mu$L Sorenson buffer, absorbance at 540 nm is read with an automated microliter plate reader. In some experiments, cells are pre-incubated for 15 minutes with P4G9 or HP2/1 (Clonetech, Palo Alto, Calif.) (anti-VLA-4), PI D6 (anti-VLA-5), or isotype antibody controls before application to wells.

Results

FN-adhered Myeloma Cells Show a Decreased Response to Doxorubicin by MTT Cytotoxicity Analysis A short-term MTT-based cytotoxicity assay is used to assess whether or not engagement of cell surface integrins can contribute to cell survival. 8226/S cells are adhered to FN-coated wells for one hour, and unbound cells are removed by aspiration and washed with serum-free media. As a control, an approximately equal cell number is added to uncoated wells or wells coated with BSA. After 24 hours, doxorubicin or melphalan is added to each well for one hour, drug-containing media is then removed and replaced by fresh media. After a 96 hour incubation, cell survival is determined by the ability of viable cells to reduce MTT dye to formazan. IC50 values are derived through linear regression of the log-linear dose-response plots for each cell line to each drug. Student's T-test is used to analyze differences in drug response using data collected from three different experiments (0.05 significance level). 8226/S myeloma cells adhered to FN-coated plates have a significant survival advantage over those grown on BSA-coated plates when exposed to doxorubicin for 1 hour following a 24 hour pre-adhesion period [FIG. 1a], (n=3, mean difference= 6.9.s.d.=5.2, range=2.4 to 12.6, P<0.05). The mean IC50 value for FN-adhered cells is 1.63 uM dox (s.d.=1.51, range=0.49 uM to 3.34 uM) compared to 0.52 uM for cells grown on BSA (n=3, s.d.=0.76, range.=0.085 uM to 1.4 uM). Subtoxic concentrations of doxorubicin often induced a mitogenic effect in FN-adhered cells (>100 percent survival. FN-adhered cells often showed a decreased response to melphalan [FIG. 1b], however this effect proved to be inconsistent (n=3, mean difference=1.7, s.d.=0.8, range= 1.2–2.6). The mean IC50 value for FN-adhered cells is 48 uM melphalan (n=3, s.d.=26 uM, range=18 uM to 65 uM), compared to 30 uM for cells grown on BSA (n=3, s.d.=20 uM, range=15 uM to 53 uM).

Annexin V Flow Cytometry Analysis of Apoptosis

As a second marker for apoptosis not based on cell growth, phycoerythrin (PE)-conjugated Annexin V is used, which recognizes inverted phosphatidylserine on the exterior of the plasma membrane as an early stage apoptotic marker.

Approximately $0.5 \times 10^6$ 8226/S cells are adhered to FN-coated or uncoated 6 well tissue culture plates for 24 hours before being exposed to either 1 uM doxorubicin or 50 uM melphalan. After a 24 hour incubation, cells are collected and the apoptotic fraction determined using Annexin V-PE staining and flow cytometric analysis. FN-adhered 8226/S cells have a lower percentage of apoptotic cells (mean=16.3 percent) compared to non-adhered controls (mean=40.3 percent) following a 1 hour doxorubicin exposure (P<0.05) [FIG. 2a]. A smaller, but statistically different (P<0.05), effect is seen with FN-adhered cells treated with 50 uM melphalan (16.53 percent vs. 21.5 percent) [FIG. 2b]. In further experiments, cells are exposed to drug prior to FN-adhesion in an attempt to rescue them from the consequent initiation of apoptosis. Annexin V staining revealed that FN adhesion is unable to rescue myeloma cells following initial exposure to doxorubicin or melphalan.

Bcl-2, Bcl-XL, Bcl-XS, and BAX mRNA Levels Are Unchanged in 8226/S Following 24 Hour Adhesion to FN An RNase protection assay is utilized to observe possible transcriptional changes in these genes, in order to determine whether expression of the Bcl-2 family members known to suppress (Bcl-2 and Bcl-XL) or promote (BAX and Bcl-XS) apoptosis are altered in FN-adhered cells. Expression levels and ratios of all Bcl-2 family members are found to be unchanged, and therefore altered RNA levels of these apoptosis regulating proteins are not likely responsible for protecting FN-adhered myeloma cells from acute cytotoxic drug exposure [FIG. 3]. To confirm these results, semi-quantitative RT-PCR for Bcl-2, Bcl-XI, Bcl-Xs, and BAX is performed on RNA collected from three different cell samples. As in the RNase protection assay, no significant changes in the levels of these genes are observed in FN-adhered cells.

Intracellular Doxorubicin Accumulation and Expression of Known Drug Transporters Are Not Altered by FN Adhesion Because active drug transport is a common mechanism of doxorubicin resistance and because in rare instances ECM adhesion can upregulate P-glycoprotein, possible reductions in intracellular drug accumulation in adhered myeloma cells are examined. A flow cytometry-based intracellular drug accumulation assay reveales that the concentration of doxorubicin, which emits at 573 nm after excitation, in FN-adhered myeloma cells is equal to that seen in non-adhered controls [FIG. 4]. Due to the fact that some drug transporters may alter nuclear drug concentration with minimal effects on total intracellular drug, RT-PCR is used to investigate whether or not three known transport proteins are upregulated by FN adhesion. Two members of the ABC superfamily of transmembrane gycoproteins, MDR1 (encoding P-glycoprotein) and MRP (encoding the multidrug resistance-associated protein), which are known to actively extrude drugs such as doxorubicin, are unchanged following FN adhesion. Expression of LRP (lung resistance-associated protein), which has also been associated with drug resistance, is also unchanged in adhered myeloma cells compared to suspension cells. In addition to ruling out altered drug transport as a mechanism of adhesion-based drug resistance, these studies also show that ECM components of the bone marrow microenvironment environmental probably do not affect the intrinsic expression of these drug transporters in human myeloma cells.

VLA-4 Is Over Expressed in Drug Resistant Variants of the 8226/S Myeloma Cell Line Low level drug resistant variants are selected from the 8226/S drug sensitive human myeloma cell line using stepwise increases in melphalan or doxorubicin over a period of approximately 10 months. The acquired resistance of the 8226/LR5 (L-phenylalanine mustard resistant) cell line is based on the overexpression of glutathione and glutathione-associated enzymes. 8226/DOX6 (doxorubicin resistant) acquired a P-glycoprotein based mechanism of resistance after chronic drug selection. Both of these cell lines are assayed for changes in cell surface integrin expression. Cell lines are incubated with monoclonal antibodies to the $\alpha_4$, $\alpha_5$, $\beta_1$ or $\beta_7$ integrin subunits, followed by labeling with a fluorescein isothiocyanate (FITC)-conjugated secondary antibody. In both 8226 cell line variants, acquired resistance to doxorubicin or melphalan is associated with an increase in $\alpha_4$ surface expression as determined by fluorescence activated cell sorting analysis [FIG. 5, table 1]. When compared to levels found in the 8226/S parent line, $\alpha_4$ subunit expression is increased 4 fold in both 8226/LR5 and 8226/DOX6 (n3). $\beta_1$ subunit expression increased 2.5 fold in 8226/LR5 while a more modest increase of 70 percent is seen in 8226/DOX6 when compared to parent cell line levels. $\beta_7$ integrin, the only other integrin subunit known to heterodimerize with $\alpha_4$, is increased 3.6 fold in 8226/LR5 but remained unchanged in 8226/DOX6. $\alpha_5$ expression levels remained relatively low in both 8226 drug selected cell lines.

TABLE 1

Fluorescence-activated cell sorter (FACS) analysis of integrin subunits on drug resistant cell lines.

| Cell line | $\alpha_4$ | $\alpha_5$ | $\beta_1$ | $\beta_7$ |
|---|---|---|---|---|
| 8226/S | 10.41 | 14.24 | 8.43 | 5.72 |
| 8226/LR5 | 46.53* | 11.95 | 44.63* | 40.21* |
| 8226/DOX6 | 69.00* | 7.32 | 26.21 | 18.49 |

Values reported are the mean fluorescence intensity of representative histograms from three different experiments. *indicates integrin subunit expression is significantly higher than 8226/S at the $P > 0.05$ level (n = 3).

Drug Sensitive Revertant Cell Lines Express $\alpha_4$ Levels Equal to that of 8226/S When removed from the drug for a period of 20 weeks, 8226/LR5 reverts back to a drug sensitive phenotype with $\alpha_4$ integrin expression comparable to the drug sensitive parent cell line 8226 [FIG. 6a]. The level of $\alpha_5$ remained low in the revertant cell line as well (data not shown). The same observations are made when 8226/DOX6 are removed from maintenance drug for 20 weeks [FIG. 6b]. These experiments demonstrate a correlation between levels of $\alpha_4$ expression and drug resistance in the 8226 myeloma cell line. Acute exposure of 8226/S to a wide range of concentrations of doxorubicin or melphalan has no immediate effects (1–48 hours) on cell surface integrin expression, as determined by FACS analysis (data not shown), suggesting a process of selection for $\alpha_4$ overexpression, rather than drug-induced upregulation of this gene.

Drug resistant 8226 Cell Lines Demonstrate Increased Levels of $\alpha_4$-mediated FN Adhesion Functionality of surface VLA-4 and VLA-5 is investigated using a fibronectin adhesion assay with pre-coated microtiter plates. BSA is used to control for non-specific cell adhesion and several monoclonal antibodies are used to inhibit $\alpha_5$ (P1D6)- and $\alpha_4$ (P4G9 and HP2/1)-mediated adhesion. Cell lines selected from 8226/S by continuous drug exposure displayed significant increases in $\alpha_4$-mediated FN binding ability [FIG. 7] compared to the parent cell line, 8226/S, which utilized both $\alpha_5$ and $\alpha_4$ for FN adherence. This class switch of integrins functioning in adherence may be indicative of an advantage in $\alpha_4$- vs. $\alpha_5$-mediated signal transduction during the selection process, although further study is needed to investigate these possibilities.

Discussion

Integrins and ECM interactions play critical roles in cell survival. During the course of initial or chronic drug exposure, myeloma cells overexpressing VLA-4 have a selection advantage over cells expressing low levels of this protein. Experiments involving the treatment of 8226/S with short term (1–48 hours) doses of doxorubicin or melphalan indicate that increases in $\alpha_4$ expression are not seen immediately, probably ruling out drug-induced transcriptional upregulation as a reason for FN receptor overexpression. Drug resistant cells removed from chronic drug exposure eventually lose their high $\alpha_4$ expression levels along with their resistant phenotype, implicating selection pressure as a prerequisite for $\alpha_4$ upregulation. This correlation between integrin expression and resistance levels is seen in both doxorubicin- and melphalan-selected variants of 8226/S.

Cells in direct contact with immobilized FN are less sensitive to acute doxorubicin treatment. A decreased response to melphalan in FN-adhered cells is not consistently observed during acute exposure using MTT cytotoxicity analysis (possibly as a result of assay insensitivity), however, significant increases in cell survival are detected using Annexin V. Although the level of cytoprotection may be small following an acute survival assay, these differences may be sufficient to give rise to a large phenotypically distinct population over the course of chronic drug exposure in vitro or in.

Soluble FN may have the capacity to induce $\beta_1$ signaling without adhesion within myeloma cell cultures. The overexpression and utilization of $\alpha_4$ for FN adhesion by drug resistant myeloma cell lines may indicate a consequent increase in the number of intercellular interactions (through FN binding, VCAM-1 binding, or homotypic $\alpha_4$ binding by tumor cells exposed to DNA damaging agents, or the increased binding of soluble FN from serum). Many cultured myeloma cell lines, including 8226, produce a relatively high amount of cell surface FN compared to normal plasma cells, an observation also seen clinically in patient specimens. DNA damaging agents such as doxorubicin or melphalan may also induce increased production of ligand, as is shown with human mesangial cell cultures and FN synthesis. Cells under selection pressure may then utilize soluble or cell-bound integrin ligands, and subsequent $\alpha_4$-mediated signalling, as a cytoprotective mechanism.

Some previously established mechanisms of drug resistance are investigated as possible causes of the cytoprotective effect of FN. Since drug transporters such as P-glycoprotein have been well documented mediators of drug resistance in myeloma cells, possible alterations in intracellular drug concentration following adhesion are investigated. FN-adhered cells are found to contain doxorubicin levels equal to those seen in non-adhered cells using standard techniques. In some cases, intracellular drug compartmentalization can be altered by P-glycoprotein without high levels of drug extrusion, for this reason the expression of three drug transporters is analzed by semi-quantitative RT-PCR The expression of MDR1, MRP, and LRP are all equal between FN-adhered and non-adhered cells, probably ruling out induction of active drug transport as a possible mechanism of cytoprotection in these experiments.

Another family of proteins known to effect apoptosis and drug response is the Bcl-2 family. VLA-5 and VLA-6 upregulate Bcl-2 and protect against apoptosis in certain cell types following ligation with FN or laminin, respectively. RNase protection and RT-PCR assays shows the RNA levels coding for this protein to be unchanged in FN-adhered cells.

Furthermore, expression levels of the anti-apoptotic protein Bcl-XL, which is upregulated in keratinocytes following adhesion, are unchanged following FN adhesion. No changes in the expression of other anti-apoptotic (Bcl-w and Mcl-1) or pro-apoptotic genes (BAX, Bcl-XS, Bad and Bik) are detected by either of these assays. However, it is also possible that integrins affect post-translational modification of these proteins and their potential participation in CAM-DR.

These investigations provide significant insight on the effects of adhesion on cell cycle kinetics and how this imparts drug resistance to tumor cells. VLA-4-mediated adhesion decreases the proliferation of hematopoietic progenitor cells and the $\alpha_4$ over expressing cell lines 8226/LR5 and 8226/DOX6 have longer doubling times in culture compared to the 8226/S parent cell line (LR5=30 hr, DOX6=39 hr, S=27 hr).

Phosphatidylinositol 3 kinase (PI3 kinase)/AKT pathway has a major influence on cellular apoptotic commitment and PI3 kinase activation inhibits apoptosis in haemopoietic cells. Thus, this pathway is a likely mechanism of apoptotic suppression in FN-adhered cells. FN adhesion and VLA-4 ligation is known to initiate the PI3 kinase signaling cascade in some cases, but VLA-4 or VLA-5 have not yet been directly correlated with this pathway in myeloma cells. Furthermore, a frequent association is observed between these integrins and FAK, a known activator of PI3 kinase. Through activation by PI3-K lipid products or by direct phosphorylation, AKT phosphorylates the Bcl-XL/Bcl-2-associated death promoter (BAD), promoting cell survival possibly by dissociating it from Bcl-XL and decreasing the amount of BAX homodimers. The endpoint of the PI3-K/AKT signaling cascade may involve an eventual blockade of ced3/ICE activity and a subsequent inhibition of tumor cell death.

In summary, integrin-mediated FN adhesion is shown to cause a decreased response to chemotherapeutic drugs as well as a correlation between the expression of $\alpha_4$ integrin heterodimers and drug resistance. The term cell adhesion mediated drug resistance, or CAM-DR, describes this observation. Two well established causes of drug resistance, active drug transport and increased expression of Bcl-2 family members, are shown not to produce these effects. Clinically, elevated FN receptor expression or function in myeloma cells within the bone marrow may be an indicator of a more aggressive tumor cell which has a survival advantage against the cytotoxic effects of anticancer drugs. In vivo alterations in fibronectin receptor expression or function may have a magnified effect on myeloma cell survival when they are in direct association with stromal cells and ECM components of the bone marrow. The cytoprotection conferred by fibronectin receptors may be low level, but intrinsic, since most myeloma cells inherently express moderate to high levels of these integrins. Small changes in drug sensitivity in vitro are probably highly relevant clinically since even a 1 percent surviving tumor fraction can have drastic long term consequences. The CAM-DR mediated by FN adhesion may be sufficient to allow the eventual emergence of drug resistance mechanisms such as upregulation of P-glycoprotein, MRP, and alterations in topoisomerase II, which then become the predominant cytoprotective processes. Therefore, specific integrin subunits and the various signal transduction elements they utilize, provide promising therapeutic targets. Established antagonists of VLA-4 and VLA-5 integrin function may serve as chemosensitizers when administered in conjunction with conventional chemotherapeutics, leading to higher levels of drug response and improved clinical outcome.

EXAMPLE TWO

Materials and Methods

Cell culture conditions

The K562 cell line is obtained from the American Type Culture Collection (Rockville, Md.). Cells are grown in suspension in RPMI 1640 medium supplemented with 5 percent fetal bovine serum, 1 percent (v/v) penicillin (100 units/ml), streptomycin (100 units/ml), and 1 percent (v/v) L-glutamnine (all from Gibco BRL, Grand Island, N.Y.). Cells are maintained at 37° C. in 5 percent $CO_2$-95 percent air atmosphere and subcultured every 6 days.

Materials

All cytotoxic drugs are obtained from Sigma-Aldrich (St. Louis, Mo.) and are dissolved in $H_2O$ except for melphalan (LPAM), which is dissolved in acidified ethanol. BCR/ABL kinase inhibitor AG957 is from Calbiochem (San Diego, Calif.) and is solubilized in DMSO. Exposure to γ-irradiation is carried out in a Mark I model 68A irradiator using a 2,200 Ci Cs source. Anti-CDw49d ($\alpha_4$) mAb P4G9, anti-CDw49e ($\alpha_5$) mAb P1D6, anti-Bcl-2 mAb clone 124, and FITC-conjugated goat-anti-mouse antibodies are all from DAKO (Carpinteria, Calif.). Anti-CD29 mAb MAR4 is from Pharmingen (San Diego, Calif.). β1 blocking Ab P4C10 is from Life Technologies (Rockville, Md.). To stimulate integrin function in some studies, anti-β1 mAb B3B11 (Chemicon, Temecula, Calif.) is used. Anti-Mcl-1 polyclonal Ab, anti-Bax polyclonal Ab, and anti-Bcl-X polyclonal Ab are from Santa Cruz Biotechnology (Santa Cruz. Calif.). Anti-phosphotyrosine mAb (4G10) is from Upstate Biotechnology (Lake Placid, N.Y.). Anti-β-actin mAb is from Sigma. HRP-conjugated goat-anti-mouse and goat-anti-rabbit antibodies are from Jackson Immunoresearch (West Grove, Pa.).

MTT cytotoxicity assays

Plastic 96-well Immunosorp plates (Nunc, Denmark) are coated with 50 μl (40 μg/ml) FN (Life Technologies) or BSA overnight. Cells are washed once and resuspended in serum-free RPMI 1640, then $2 \times 10^4$ (K562) cells are added to each FN coated well. $8 \times 10^3$ (K562) cells are added to BSA coated wells. Cells are incubated for 2 hours at 37° C., washed with serum free media, and put back into serum-containing media Following 24 hours in a tissue culture incubator, drug or vehicle control is added to each well for 90 minutes, media is removed and replaced with drug-free media for 96 hours. In some experiments, the drug is allowed to remain in each well for 96 hours. 50 μl 3-[4,5-Dimethylthiazol-2-yl]-2,5-diphenyltetrazolium bromide; Thiazolyl blue (MTT dye) (Sigma) is added to each well for 4 hours, plates are centrifuged and each well aspirated. Dye is solubilized with 100 μl DMSO and plates are read at 540 nm on an automated microtiter plate reader. A blank well containing only medium and drug is also run as a control in all experiments. IC50 values are calculated by linear regression analysis of percent survival vs. drug concentration.

Annexin V apoptosis analysis

For each replicate, $1 \times 10^6$ cells are attached to 35 mm dishes (Nunc) coated overnight with 1 ml of 40 μg/ml FN. In some experiments, cells are pre-incubated with β1 stimulating mAb B3B11 for 15 minutes at 37°, then are incubated with α4 or α5 blocking antibody for an additional 15 minutes prior to attachment. After two hours, non-adhered cells are removed from plates with serum-free media washes. Cells are exposed to drug for 90 minutes (plus a 24 hour drug-free incubation period) or for 24 hours continuously. As a control, $0.4 \times 10^6$ cells are drug treated in suspension and then plated on uncoated 35 mm dishes. Cells are then collected using gentle agitation, washed, and are incubated with FITC-conjugated Annexin V (BioVision, Palo Alto, Ca). 5000–10000 events are analyzed on a FACScan machine (Becton-Dickinson, San Jose, Calif.) and percent apoptosis is determined using CellQuest software (Becton-Dickinson).

Integrin expression analysis

Cells are washed once with cold PBS, incubated with primary antibody or an isotype control for 30 minutes on ice, washed two times with PBS, then incubated with FITC-conjugated goat anti-mouse secondary antibody for 30 minutes. Following two washes with PBS, FL-1 fluorescence is analyzed by a FACScan machine, which recorded 10,000 events for each analysis.

Adhesion assays

Cellular adhesion to FN is determined. In some experiments, cells are pre-incubated for 15 minutes with P4G9, P1D6, B3B11, or isotype antibody controls prior to application to wells.

Western blotting

Approximately $5 \times 10^6$ cells are centrifuged, resuspended in serum-free RPMI, and adhered to 60 mm FN-coated plates (3 ml of 40 µg/ml FN is used). Control cells are kept in serum-free media in conical tubes (equal density) for a period of time equal to the adhesion time. Non-adherent cells are gently washed 2–3 times with serum-free media and cells are placed back into media containing 5 percent FBS. Cells are lysed in ice cold modified RIPA buffer (50 mM Tris-HCl pH 7.5, 150 mM NaCl, 1 percent NP-40, 0.5 percent sodium deoxycholate, 0.1 percent SDS) containing fresh protease and phosphatase inhibitors (2 µg/ml aprotinin, 2 µg/ml leupeptin, 2 mM PMSF, 20 mM NaF, 1 mM sodium vanadate, 10 mM sodium pyrophosphate, 20 mM β-glycerophosphate). Lysates are cleared by centrifugation, and quantitated using the BCA protein assay (Pierce, Rockford, Ill.). Equivalent amounts of protein are combined with 6xSDS Laemelli loading dye, boiled for 3 minutes, then separated by 10 percent SDS-PAGE. Proteins are transferred to PVDF membrane (Bio-Rad, Richmond, Calif.) overnight, after which membranes are blocked in PBS containing 5 percent dry milk and 0.01 percent tween-20 (Bcl-2 family and β-actin immunoblotting) or PBS containing 3 percent milk for 2 hours (phosphotyrosine immunoblotting). Membranes are incubated with primary antibodies and washed as per manufacturer's protocol, then incubated with horse radish peroxidase (HRP)-conjugated goat-anti-mouse or goat-anti-rabbit secondary antibodies for 1 hour. Proteins are visualized using Lumi-Light substrate (Boehringer Mannheim, Indianapolis, Ind.) and X-ray film (Kodak). To assay for equal protein loading, membranes are stripped for 30 minutes at 50° C. in stripping buffer (62.5 nM Tris-HCl pH 6.8, 2 percent SDS, 100 mM 2-mercaptoethanol), re-blocked, and probed with anti-β-actin mAb.

RNase protection assay

RNase protection assays are performed. Bcl-2 family specific probes are synthesized using a template set from Riboquant (San Diego, Calif.). Expression of mRNA corresponding to Bcl-2, Bcl-XI, Bcl-Xs, BAX, Bik, Bad, Bcl-w, Bak, Mcl-1 and Bfl1 is quantitated by normalizing to GAPDH and L32 expression.

α4 vector construction and transfection

The full-length cDNA encoding the human α4 integrin subunit (accession #X16983) is obtained from ATCC in a Bluescript plasmid. The 3.87 KB alpha4 insert is cut out of the plasmid, run on a 1 percent low melting point agarose gel, stained with ethidium bromide, and cut out and purified using a gel purification kit (Qiagen, Valencia, Calif.). The insert is then treated with alkaline phosphatase (Boehringer Mannheim) and ligated into the multiple cloning site of pcDNA3.1(+) (Invitrogen, San Diego, Calif.) using T4 DNA polymerase (Invitrogen). Bacteria are transformed and colonies are selected for mini-prep analysis. Vectors are checked for correct orientation of insert using restriction digests and inserts are sequenced by the molecular biology core (Moffitt Cancer Center). K562 cells are split one day prior to transfection. $2 \times 10^6$ cells are washed once with PBS and then seeded into a 60 mm dish (Nunc) in 4 ml of RPMI 1640/5 percentFBS/1 percent Pen/Strep. 5 µg of vector DNA (pcDNA3.1 or pcDNA3.1/alpha4) dissolved in TE buffer (pH 7.4) is combined with serum-free media to make a total volume of 150 µl. 20 ml of Superfect reagent (Qiagen) is then added and the mixture is vortexed for 10 seconds. Following a 10 minute incubation at room temperature, 1 ml of media containing serum and antibiotics is added to the mixture which is then added dropwise to 60 mm dishes with cells. 48 hours after transfection, cells are seeded into T75 flasks (Falcon) and stable transfectants are selected by adding 1000 µg/ml G418 (Genetecin, Life Technologies) to the culture medium for approximately four weeks. α4 expression is analyzed by flow cytometry and to select for a more homogenous population, pcDNA3.1/α4 and pcDNA3.1 transfected cells are subcloned using a limiting dilution technique. All clones from K562/pcDNA3.1 are negative for α4 expression by flow cytometery and 3 clones from the K562/α4 population are positive. These three clones from each line are mixed to create the cell lines K562/pcDNA3.1 (empty vector transfected) and K562/VLA-4 (α4 transfected).

RT-PCR for a4 Integrin subunit expression

Total cellular RNA is collected from $3 \times 10^6$ cells using TRIzol reagent (Gibco). RNA is quantitated on a spectophotometer at 260 nm. cDNA is synthesized in a 20 ul reverse transcription reaction containing 100 ng RNA, 1xPCR Buffer (10 mM Tris, pH 8.3–50 mMKCL-1.5 mM $MgCl_2$), 1 mM concentrations each of dATP, dGTP, dCTP, and dTTP; 100 pmol random hexamers, 20 units RNAse inhibitor, and 6 units avian megalovirus reverse transcriptase (Boeringer-Mannheim). The reaction is prepared on ice then incubated at 42° C. for 1 hour, 99° C. for 10 minutes, and quick chilled to 4°. The following primers are synthesized (Gibco/BRL) and used for α4-specific PCR reactions: 5'-ATGGCTCCCAATGTTAGTGTGG-3' (upstream) (SEQ ID NO:3) and 5'-CACTGGCTTCTTTTCCACTTTCC-3' (downstream) (SEQ ID NO:4). The 292 base pair α4 product is amplified using 20 µl of PCR reaction mixture (1xPCR buffer, 6.25 pmol of α4 specific amplimers), 0.5 units Taq polymerase (Boehringer-Mannheim), and 5 µl of cDNA. Samples are subjected to incubation at 94° C. for 1 minute and then 34 cycles of 94° C. (15 sec), 72° C. (15 sec), and a final extension at 72° C. for 1 minute in a thermal cycler (Perkin-Elmer Cetus). Histone 3.3 is amplified and used as a control for RNA integrity and quantity. Samples are loaded on a 3 percent agarose gel, electrophoresed one hour at 80V, and visualized using EtBr staining. Restriction digests are used to confirm identity of products.

Results

K562 Cells Are Resistant to Drug-induced Apoptosis when Adhered to FN

The MTT assay is used to detect differences in the drug sensitivity of FN adhered vs. suspension-cultured cells following a 90 minutes or 96 hours (continuous) exposure to either mitoxantrone or melphalan (L-phenylalanine mustard or LPAM). After a 96 hour period in a cell incubator, cell survival is determined by the ability of viable cells to reduce MTT dye to formazan. IC50 values are derived through linear regression of the log-linear dose-response plots for each cell line to each drug. Student's T-test is used to analyze differences in drug response using data collected from at least three different experiments. FIGS. 8A and 8B depict representative continuous exposure experiments using mitoxantrone and LPAM, respectively.

Table 2 summarizes IC50 values, standard deviations, and fold differences. FN adhered K562 cells exposed to the topoisomerase II inhibitor mitoxantrone for 90 minutes are approximately 3.7 fold resistant when compared to suspension treated cells (p<0.05; mean IC50 suspension=$2.06 \times 10^{-7}$M, s.d.=1.62, n=4, range=$1.5 \times 10^{-8}$M to $4.04 \times 10^{-7}$M; mean IC50 FN=$7.67 \times 10^{-7}$M, s.d.=4.49, n=4, range=$5.2 \times 10^{-7}$ M to $1.44 \times 10^{-6}$M). Under continuous exposure, FN adhered cells are 6.8 fold more resistant to mitoxantrone compared to suspension grown cells (p<0.05; mean IC50 suspension=$4.79 \times 10^{-8}$M, s.d.=1.64, n=3, range=$3.78 \times 10^{-8}$M to $6.68 \times 10^{-8}$M; mean IC50 FN=$3.27 \times 10^{-7}$M, s.d.=3.00, n=5, range=$1.62 \times 10^{-8}$M to $6.69 \times 10^{-7}$M). FN adhered cells are approximately 6.5 fold more resistant to LPAM treatment (90 minutes) compared to suspension grown cells (p<0.05; mean IC50 suspension=2.93, s.d.=70, n=5, range=$1.48 \times 10^{-5}$M to $5.14 \times 10^{-5}$M; mean IC50 FN=$1.90 \times 10^{-4}$M, s.d.=1.09, n=5, range=$5.85 \times 10^{-5}$M to $3.4 \times 10^{-4}$M). Following a continuous exposure to LPAM, FN adhered cells are 2.25 fold more resistant than suspension cells (p<0.10; mean IC50 suspension=$2.55 \times 10^{-5}$M, s.d.=1.42, n=5, range=$1.06 \times 10^{-5}$M to $4.32 \times 10^{-5}$M; mean IC50 FN=$5.73 \times 10^{-5}$M, s.d.=3.43, n=5, range=$2.32 \times 10^{-5}$M to $1.04 \times 10^{-4}$M).

TABLE 2

|  | LPAM- 90 min. exposure | LPAM- continuous exposure | Mitoxantrone- 90 min. exposure | Mitoxantrone- continuous exposure |
| --- | --- | --- | --- | --- |
| Suspension mean IC50 | $2.93 \times 10^{-3}$M (+/−1.70) | $2.55 \times 10^{-5}$M (+/−1.42) | $2.06 \times 10^{-7}$M (+/−1.62) | $4.79 \times 10^{-8}$M (+/−1.64) |
| Fibronectin mean IC50 | $1.90 \times 10^{-4}$M (+/−1.09) | $5.73 \times 10^{-5}$M (+/−3.43) | $7.67 \times 10^{-7}$M (+/−4.49) | $3.27 \times 10^{-7}$M (+/−3.00) |
| Fold resistance | 6.48 | 2.25 | 3.72 | 6.83 |

As a second method for determining cell survival, an Annexin V flow cytometric based assay is employed. Cells are seeded onto dishes coated with FN, poly-L-lysine (PLL), or BSA (or are kept in suspension) for 2 hours in serum-free media, exposed to drug for 90 minutes, washed, and incubated drug-free for an additional 24 hours. In some experiments, cells are exposed to drug for 24 hours (continuous exposure). The percent of apoptotic cells is then determined by staining with Annexin V, which recognizes inverted phosphatidyl serine on the external surface of the cell as an early apoptotic marker.

FIG. 9 demonstrates that FN adhesion confers significant protection from apoptosis induced by LPAM exposure. In these experiments, BSA is used as a control for non-specific protein interactions and PLL is used as a control for non-specific cell adhesion. Neither of these substrates confers a survival advantage to cells when compared to those treated in suspension. It is interesting to note that the addition of soluble FN to conditioned serum-free culture media does not cause a consistent suppression of drug-induced apoptosis, suggesting the CAM-DR phenotype requires both ligand occupancy of the FN receptor and integrin-specific cell adhesion. Table 3 summarizes drug and radiation responses of K562 cells adhered to FN vs. grown in suspension. Significant cytoprotection is primarily observed for DNA damaging agents (FN-mediated protection against the microtubule inhibitor vincristine is not significant). FN adhesion also afforded a higher degree of protection following acute (90 minutes) exposure to drug when compared to continuous exposure. Vincristine and Ara-C are only used in continuous exposure experiments due to the inherent insensitivity of K562 cells to these compounds.

TABLE 3

| Treatment | Suspension: mean death | FN: mean death | % Control death |
| --- | --- | --- | --- |
| LPAM 100$_\mu$M 1 hr | 37.5 ± 24.0 | 11.0 ± 8.3 | 29.3* |
| LPAM 100$_\mu$M cont. exp. | 39.8 ± 3.2 | 23.3 ± 6.4 | 58.5* |
| Mitox 50$_\mu$M 1 hr | 46.3 ± 8.4 | 27.0 ± 9.4 | 58.3* |
| Mitox 10$_\mu$M cont. exp. | 42.8 ± 8.4 | 29.7 ± 6.2 | 69.4* |
| VCR 10$_\mu$M cont. exp. | 17.8 ± 6.4 | 12.5 ± 2.3 | 70.2 |
| Ara-C 100$_\mu$M cont. exp. | 11.3 ± 5.5 | 6.2 ± 1.6 | 54.9* |
| XRT 5000 rads | 32.3 ± 5.5 | 26.4 ± 3.6 | 81.7* |

Generation and Characterization of Stable VLA-4 Transfectants

Although the K562 cell line expresses only the VLA-5 FN receptor, CML cells from patients also express the VLA-4. Other cell types also show the anti-apoptotic potential of VLA-4. For these reasons, an α4 positive K562 cell line is created for use in subsequent experiments. A vector containing the full coding sequence for the human α4 integrin subunit is created and transfected into the K562 cell line. As a control, another population of K562 cells is also transfected with an empty vector construct (pcDNA3.1). Following a 4 week culture period with Geneticin (G418) to select for stable positive transfectants, cell populations are analyzed by flow cytometry for cell surface integrin expression. A limiting dilution assay is then used to subclone both high α4 expressing and α4 negative cell lines. Three independent positive and negative clones are grown to confluency and pooled to make the K562/VLA-4 and K562/pcDNA3 cell lines, respectively.

FIG. 10A shows cell surface expression of both the β1 and α5 integrin subunits on the surface of both cell lines but the presence of α4 only on the K562/VLA-4 cell line. RT-PCR using α4 specific primers shows that the α4 message is only detectable in the K562/VLA-4 cell line (FIG. 10B).

The ability of transfected cell lines to adhere to FN through various integrin subunits is determined using a colorimetric cell adhesion assay and function-blocking antibodies to ⊕1, α4 and α5. Cells are pre-incubated with integrin-specific antibodies or control antibodies (non-specific mouse IgG) and then seeded onto FN coated 96 well plates for 90 minutes. Although a high level of VLA-4 is expressed on the surface of K562/VLA-4, these cells are incapable of adhering to FN through α4, indicating that VLA-4 is in an inactive conformation. Addition of a β1-stimulating to mAb (clone B3B11) is necessary to induce VLA-4-mediated FN adhesion in K562/VLA-4 but not K562/pcDNA3.1 (FIG. 11). Incubation with α4 blocking antibody does not significantly reduce FN adhesion in either cell line, indicating that this subunit is either not expressed (in the case of K562/pcDNA3.1) or is not required for adhesion in the presence of the overabundance of VLA-5 (K562/VLA-4). Incubation with α5 blocking antibody blocked almost all adhesion of K562/pcDNA3.1 to FN but only slightly reduced the adhesive capacity of K562/VLA-4. These experimentsshow that K562/pcDNA3.1 adheres to FN solely through VLA-5 (as does the K562 parent cell line), while K562/VLA-4 utilizes both VLA-4 and VLA-5 for FN adhesion.

Contribution of α4 and α5 to CAM-DR in K562

K562/pcDNA3.1 and K562/VLA-4 cells are incubated with mAb B3B11 and anti-α4 or anti-α5 blocking Ab prior to adhesion to FN coated 35 mm dishes to determine whether or not α4 can contribute to CAM-DR in addition to α5 in CML cells. Following a two hour adhesion period, plates are washed with serum-free media (suspension control cells also washed), and media containing 100 μM LPAM or Acid-OH vehicle control is then added to each sample for 90 minutes and cells are then incubated for an additional 24 hours. Apoptosis is analyzed using Annexin V staining and flow cytometry. As can he seen in FIG. 12, K562/VLA-4 cells adhering through both α4 and α5 integrins demonstrate a level of cytoprotection (in comparison to drug treated suspension cells) equivalent to K562/pcDNA3.1 cells adhered through α5 alone (30.0±1.5 percent vs. 29.9±5.3 percent). When incubated with α4 blocking antibody prior to FN adhesion, both cell lines still demonstrated significant protection against melphalan-induced apoptosis (28.4±5.0 percent vs. 29.6±2.3 percent). However, when incubated with a blocking antibody prior to adhesion, the K562/pcDNA3.1 cells became sensitized to drug whereas the K562/VLA-4 cells remained significantly resistant (0±11.1 percent vs: 20.6±1.9 percent). It can be concluded that VLA-5 and VLA-4 are capable of inducing cytoprotection in K562 cells through similar mechanisms since the effects of both integrins are not additive compared to either one alone. CD34+CML cells are known to express both of these integrins in vivo and it can be inferred that if either are functional, the CAM-DR phenotype may be initiated through their common β1 integrin chain.

FN Adhered K562 Cells Are Resistant to Apoptosis Induced by BCA/ABL Kinase Inhibition The tyrphostin AG957 is used as a specific inhibitor of the p210$^{bcr-abl}$ kinase to investigate the effects of integrin-mediated FN adhesion on cell death following inhibition of the BCR/ABL cell survival pathway. The MTT cytotoxicity assay is again utilized to assess sensitivity to this compound in FN adhered vs. suspension-grown K562 cells. FIG. 13 is a representative curve showing the high degree of cytoprotection afforded by FN adhesion following exposure to AG957. From three independent experiments, the mean IC50 value for suspension grown cells is $3.60 \times 10^{-6}$ M (s.d.= 2.74, range=$7.90 \times 10^{-7}$ M to $6.27 \times 10^{-6}$ M) compared to $12.95 \times 10^{-6}$ M (s.d.=3.53, range=$9.56 \times 10^{-6}$ M to $16.60 \times 10^{-6}$ M) for FN adhered cells. These values are significantly different at the p<0.05 level (by Student's t-test) and the fold resistance of FN adhered cells over suspension cells is 3.6.

BCR/ABL-associated Tyrosine Kinase Activity Is Not Reconstituted by Integrin-Mediated Signaling The BCR/ABL protein is responsible for the constitutive phosphorylation of many kinases associated with integrin-mediated signaling K562 cells adhered to FN have a higher survival rate than suspension grown cells following AG957 treatment This leads to the hypothesis that VLA-5 is causing cell survival by substituting for BCR/ABL and inducing the activation of proteins such as p125FAK, p130Cas, PI-3 kinase, paxillin, and c-Abl. A temporal analysis of phosphotyrosine containing proteins by western blotting demonstrates that there is no further increase in the activity of kinases already active due to BCR/ABL, with the exception f an unknown 80 kDa protein (FIG. 14). Following a 4 hour treatment with 20 μM AG957, BCR/ABL associated tyrosine phosphorylation is completely abrogated in suspension cells (FIG. 15). In AG957 treated cells, FN adhesion does not reconstitute the phosphotyrosine pattern seen in untreated cells, however the 80 kDa band persists, albeit to a lesser extent. These results indicate that the mechanism of CAM-DR in K562 is independent of the BCR/ABL survival pathway, or at least the portion initiated by tyrosine kinase activation.

FN Adhered K562 Cells Maintain the CAM-DR Phenotype During AG957 Exposure

With the exception of an unknown 80 kDa protein, FN adhered cells do not induce noticeable tyrosine phosphorylation following AG957 treatment (FIG. 15). It is unclear whether or not FN adhered cells would still be resistant to drug-induced apoptosis following AG957 exposure. Cells are adhered to FN or kept in suspension for 3 hours, then exposed to AG957 (10 or 20 μM) or DMSO vehicle control for 1 hour, and then treated with 100 μM LPAM or vehicle control for 90 minutes. Apoptosis is analyzed by Annexin V staining 24 hours later. As can be seen in FIG. 16, the CAM-DR phenotype is maintained even when FN adhesion is followed by AG957 treatment. Integrin activation is sufficient to protect K562 cells from the BCR/ABL inhibitor alone (Acid-OH LPAM controls) and in combination with the alkylating agent. These results further support the finding that integrin-induced cytoprotection is mediated through signaling events independent of the tyrosine kinases activated by BCR/ABL.

Discussion

Myeloma cells adhered to FN are resistant to drug-induced apoptosis. Similarly, small cell lung cancer cells adhered to FN, collagen, and laminin are resistant to cytotoxic agents. Tumor cell-ECM interactions are also critical determinants in the survival of chronic myelogenous leukemia cells. K562 cells adhered to FN are significantly resistant to apoptosis induced by a number of DNA damaging agents including LPAM, mitoxantrone, and γ-irradiation. Non-specific, charge-based adhesion to poly-L-lysine coated surfaces did not result in decreased drug response. In addition, soluble FN added to culture medium did not provide a survival advantage to drug treated cells. These results indicate a requirement for both receptor occupancy by FN as well as physical attachment by the cell in order for cell adhesion mediated drug resistance (CAM-DR) to occur. It remains to be determined which cytoskeletal elements may be required for a cytoprotective signal to be initiated when cells become adherent.

When compared to drug sensitive myeloma cells, drug resistant cells overexpress the integrin VLA-4 on their cell surface, indicating this integrin heterodimer may be critical for the emergence of a drug resistant cell population. VLA-4 may also have importance with regard to the survival of B and T cells. CAM-DR is mediated by VLA-5 in K562 cells which are VLA-4 negative). It would thus be useful to determine if VLA-4 could be cytoprotective in these cells and whether a combination of FN receptor subtypes could lead to enhanced cell survival above and beyond that mediated by either receptor alone. Since CML cells isolated from patients are known to express both VLA-4 and VLA-5, this information could prove to be useful for the future application of pharmacological inhibitors against α4, α5, or β1 integrin subunits in this disease.

When adhered to FN, K562/pcDNA3.1 cells (expressing only VLA-5) and K562/VLA-4 cells (expressing both VLA-5 and VLA-4) are found to have comparable responses when treated with LPAM. Blocking antibody experiments also demonstrate that VLA-4 by itself could also be cytoprotective in K562 cells. It can therefore be concluded that each of these integrins share similar signaling capabilities likely based on their common β1 subunit.

The BCR/ABL kinase is believed to be critical to the survival of CML cells through its effects on a number of signal transduction pathways. Inhibitors of this fusion protein show promise as apoptosis-inducing drugs in CML cells. BCR/ABL inhibition by relatively high doses of the tyrphostin AG957 can have negative effects on FN adhesion. At the concentrations of inhibitor used in cytotoxicity assays, the adhesion of K562 cells to FN is not affected by more than 20–40 percent.

In addition to the cytotoxic agents examined, K562 CML cells are found to be resistant to the BCR/ABL inhibitor AG957 when adhered to FN. These observations show that integrins, in at least the K562 cell line, may signal through tyrosine kinases similar to those activated by BCR/ABL, effectively reconstituting the survival pathway inhibited by AG957. In some instances, when activated through FN adhesion, integrins are known to mimic many of the aspects of BCR/ABL signaling through the recruitment of c-Abl. Proteins such as p125FAK, p130Cas, paxillin, and PI3-kinase are activated (through tyrosine phosphorylation) by both BCR/ABL and β1 integrins independently. Therefore, FN adhesion allow K562 cells to survive BCR/ABL inhibition by substituting as the initiator of this survival pathway. However, it is discovered that the tyrosine phosphorylation pattern induced by the BCR/ABL kinase is completely abrogated by AG957 in both suspension and FN adhered cells (FIG. 8), indicating that integrin ligation is providing a survival signal independent of this group of signaling proteins. A protein band of approximately 80 kDa is activated by FN adhesion and persisted, to a lesser degree, in AG957 treated cells. Note that this protein is affected as well by AG957, possibly indicating a degree of non-specificity of this compound. Although these experiments rule out the integrin-induced activation of focal adhesion proteins such as FAK (125 kDa), p130Cas (125 and 115 kDa), paxillin (65 kDa) and c-Abl (145 kDa), other β1 integrin-activated proteins that are not detected by phosphotyrosine analysis, such as serine/threonine phosphorylated proteins, may contribute to the CAM-DR phenotype.

γ-irradiation and drugs such as melphalan, mitoxantrone, and AG957 induce apoptosis through different means. The ability of β1 integrins to protect cells from apoptosis induced by such a wide range of functionally distinct agents suggests a block in the initiation or execution of apoptosis at a point of general convergence. The Bcl-2 family of proteins fits the profile of general regulators of apoptotic commitment and these proteins are affected by integrin activation. An RNase protection assay demonstrates no consistent changes in the levels of RNA pertaining to any one of ten Bcl-2 family member genes in FN adhered K562 cells. In addition, the protein levels of Bcl-2, Bcl-Xl, Bax, and Mcl-1 are not altered by FN adhesion in K562 cells. This is consistent with findings reported for the RPMI 8226 myeloma cell line.

The ECM protein FN has been found to play a key role in the survival of a number of hematopoietic cell lines under conditions of cytotoxic stress. CML cells remaining in contact with the bone marrow may form the basis of a tumor cell population that is resistant to the apoptosis-inducing effects of chemotherapy. The cellular changes induced by the VLA-4 and VLA-5 integrin molecules seem to be mediated by β1 since each of these receptors are capable of providing cytoprotection, but not additively. In vitro, the CAM-DR phenotype also allows cells to survive the apoptosis-inducing actions of AG957, a specific inhibitor of the BCR/ABL kinase. AG957 is able to disrupt the tyrosine phosphorylation of all proteins activated by the BCR/ABL kinase in K562 cells at relatively low concentrations, leading to cell death. Integrin activation, despite providing protection against BCR/ABL inhibition, did not result in the phosphorylation of any of these proteins. Finally, it is determined that FN adhered K562 cells remain resistant to melphalan following AG957 exposure, a further indication that the mechanism of CAM-DR is independent of proteins within the BCR/ABL cell survival pathway. In conclusion, β1 integrins implicated in the induction of drug resistance of K562 CML cells, among other hematopoietic cell lines. Small molecule antagonists against the β1 integrin subunit therefore will prove beneficial as chemosensitizers in the treatment of cancer.

In order to further illustrate the present invention and the advantages thereof, the following additional examples are given, it being understood that same are intended only as illustrative and in no way limitative.

EXAMPLE THREE

A pre-established microtiter adhesion assay is used to determine if peptides such as RZ-3 are effective at preventing adhesion of myeloma cells to FN. The peptide RZ-3 contains all D-amino acids, and has the sequence:

kviywkag (SEQ ID NO:6)    (RZ-3)

in which the conventional one-letter code is used and lower case designates a D-amino acid, and the sequence is written from the N-terminus to the C-terminus.

Peptide variants of varying composition are examined for inhibiting tumor cell adhesion to FN and other bone marrow matrices. VLA-4 and VLA-5 are shown to play a major role in maintaining hematopoietic cells within the bone marrow and for keeping myeloma cells in an environment which promotes tumor growth and/or blocks apoptosis.

EXAMPLE FOUR

To determine if peptides such as RZ-3 are able to sensitize pre-adhered myeloma cells to cytotoxic drugs in-vitro, cells are exposed to various concentrations of peptides both before and after adhesion to FN and exposure to cytotoxic drugs. Changes in the percentages of cells undergoing apoptosis are examined by using MTT based cytotoxicity assays and Annexin V flow cytometric analysis.

EXAMPLE FIVE

To determine if peptides are able to prevent or reverse FN induced G1 cell to cycle arrest cells allowed to adhere for 24 to 48 hours before the addition of the peptide. Cell cycle arrest is detected using propidium iodide and BudR cell cycle analysis as measured by flow cytometry. Presumably malignant cells are already attached to the extracellular matrix before treatment with chemotherapy. Thus, the most effective agents will reverse, as well as prevent, cell adhesion to FN.

EXAMPLE SIX

To investigate the effect of peptides in disrupting β1 mediated signal transduction in myeloma cells the effects of peptides on Bcl-xl expression in myeloma cells is measured using western blot and RTIPCR analysis. Results indicate that FN mediated adhesion is capable of upregulating Bcl-xl expression in myeloma cells which could block apoptosis.

CONCLUSION

The present invention addresses the problem of chemotherapy and radiation induced drug resistance and describes methods for enhancing the efficacy of both cytotoxic drugs and radiation in the treatment of cancer.

The tumor cell microenvironment influences the way a tumor cell behaves and responds to cytotoxic drugs. The microenvironment can enhance tumor cell survival and prevent drug-induced apoptosis. This interaction between tumor cell and environment explains how some tumor cells survive initial drug exposure and eventually express classical mechanisms of drug resistance. Two different forms of tumor cell-environment interaction are disclosed. In the first form, soluble chemical modulators, such as cytokines, are secreted by non-tumor, stromal cells. These soluble modulators interact with tumor cell surface receptors, which in turn activate signal transduction pathways that enhance tumor cell survival and prevent apoptosis. Interleukin-6 appears to be a classical example of a soluble modulator secreted by the tumor microenvironment capable of increasing tumor cell survival and preventing apoptosis. Approaches to block signal transduction pathways mediated by IL-6, or other soluble modulators of apoptosis, can enhance cytotoxic drug activity.

In the second form of tumor cell-environment interaction, direct tumor cell contact with other cells or the ECM is associated with drug resistance. This form of drug resistance has been given the term cell adhesion mediated drug resistance (CAM-DR). To date, $\beta 1$ integrin adhesion and activation mediates the most well characterized CAM-DR phenotype. Other cell adhesion molecules are also likely to play a role in the CAM-DR phenotype. Interrupting this cell adhesion, or the signal transduction pathways associated with it, represents a new drug target for the treatment of cancer.

These two forms of tumor cell-environment interaction are illustrated by FIG. 28.

In summary, it is herein disclosed that cancer cell interaction with the extracellular matrix, including fibronectin and collagen, prevents cell death (apoptosis) induced by cytotoxic drugs and radiation, a phenomenon described as "Cell Adhesion Mediated Drug Resistance" (CAM-DR). Further, it is disclosed that integrin-mediated adhesion, including $\alpha_4\beta_1$ and $\alpha_5\beta_1$ for fibronectin and $\alpha_2\beta_1$ for collagen, prevents both drug and radiation induced cancer cell death. Therefore, integrin-mediated adhesion confers a survival advantage to cancer cells that have been exposed to drugs or radiation.

It is also shown that specific agents including peptides such as the synthetic D-amino acid peptide RZ-3 can be utilized to inhibit integrin-mediated cell adhesion thereby rendering cancer cells more sensitive to chemotherapeutic agents. Thus, integrin-mediated cell adhesion confers resistance to chemotherapeutic agents and represents a novel and specific target for the development of therapies that can interfere with or inhibit CAM-DR. Furthermore, inhibition of CAM-DR has the potential to enhance treatment responses by sensitizing cancer cells to both chemotherapy and radiation therapy.

In particular, the use of peptides (such as RZ-3) for inhibiting adhesion and enhancing the efficacy of chemotherapeutic and/or radiation treatments in the treatment of cancer is disclosed.

In a preferred embodiment, the peptide is administered prior to the administration of chemotherapy and/or radiation.

References cited through this application are each herein incorporated in their respective entireties.

While the invention has been described in terms of various preferred embodiments, those skilled in the art will recognize that various modifications, substitutions, omissions and changes may be made without departing from the spirit of the present invention. Accordingly, it is intended that the scope of the present invention be limited solely by the scope of the following claims.

What is claimed is:

1. A method for inhibiting cell adhesion mediated drug resistance in a patient in need thereof, said method comprising administering to the patient an effective amount of a peptide that inhibits cell adhesion mediated drug resistance, wherein the peptide comprises the amino acid sequence of SEQ ID NO:6, or a pharmaceutically acceptable salt or variant thereof, and wherein the variant has at least one of the following characteristics: the variant contains one or more hydroxyproline or hydroxylysine; the variant contains an organic acid or amide; the variant contains a C-terminal carboxylate; the variant is esterified; the variant is amidated; the variant has a modified N-terminal amino group; the variant has a side-chain modification or substitution selected from the group consisting of methylation, benzylation, t-butylation, tosylation, and alcoxycarbonylation; the variant has an N-acetyl group; the variant has a C-terminal amide group; or the variant has an amino acid selected from the group consisting of penicillamine, tetramethylene cysteine, pentamethylene cysteine, mercaptopropionic acid, pentamethylene-mercaptopropionic acid, 2-mercaptobenzene, 2-mercaptoaniline, 2-mercaptoproline, ornithine, diaminobutyric acid, aminoapidic acid, m-aminomethylbenzoic acid, and diaminopropionic acid.

2. The method of claim 1, wherein the peptide comprises the amino acid sequence of SEQ ID NO:6, or a pharmaceutically acceptable salt thereof.

3. The method of claim 1, wherein the peptide comprises the amino acid sequence of SEQ ID NO:6.

4. A method for enhancing the efficacy of chemotherapy or radiation therapy in a patient in need thereof, said method comprising administering an effective amount of a peptide that inhibits cell adhesion mediated drug resistance in the patient; and administering chemotherapy, radiation therapy, or both, to the patient; whereby the efficacy of the therapy is enhanced and wherein the peptide comprises the amino acid sequence of SEQ ID NO: 6, or a pharmaceutically acceptable salt or variant thereof, wherein the variant has at least one of the following characteristics: the variant contains one or more hydroxyproline or hydroxylysine; the variant contains an organic acid or amide; the variant contains a C-terminal carboxylate; the variant is esterified; the variant is amidated; the variant has a modified N-terminal amino group; the variant has a side-chain modification or substitution selected from the group consisting of methylation, benzylation, t-butylation, tosylation, and alcoxycarbonylation; the variant has an N-acetyl group; the variant has a C-terminal amide group; or the variant has an amino acid selected from the group consisting of penicillamine, tetramethylene cysteine, pentamethylene cysteine, mercaptopropionic acid, pentamethylene-mercaptopropionic acid, 2-mercaptobenzene, 2-mercaptoaniline, 2-mercaptoproline, ornithine, diaminobutyric acid, aminoapidic acid, m-aminomethylbenzoic acid, and diaminopropionic acid.

5. The method of claim 4, wherein the peptide comprises the amino acid sequence of SEQ ID NO:6, or a pharmaceutically acceptable salt thereof.

6. The method of claim 4, wherein the peptide comprises the amino acid sequence of SEQ ID NO:6.

7. A method for treating cancer in a patient in need thereof, said method comprising administering an effective amount of a peptide to the patient to inhibit cell adhesion mediated drug resistance in the patient; and administering chemotherapy, radiation therapy, or both, to the patient; and wherein the peptide comprises the amino acid sequence of SEQ ID NO: 6, or a pharmaceutically acceptable salt or variant thereof, wherein the variant has at least one of the following characteristics: the variant contains one or more hydroxyproline or hydroxylysine; the variant contains an organic acid or amide; the variant contains a C-terminal carboxylate; the variant is esterified; the variant is amidated; the variant has a modified N-terminal amino group; the variant has a side-chain modification or substitution selected from the group consisting of methylation, benzylation, t-butylation, tosylation, and alcoxycarbonylation; the variant has an N-acetyl group; the variant has a C-terminal amide group; or the variant has an amino acid selected from the group consisting of penicillamine, tetramethylene cysteine, pentamethylene cysteine, mercaptopropionic acid, pentamethylene-mercaptopropionic acid, 2-mercaptobenzene, 2-mercaptoaniline, 2-mercaptoproline, ornithine, diaminobutyric acid, aminoapidic acid, m-aminomethylbenzoic acid, and diaminopropionic acid.

8. The method of claim 7, wherein the peptide comprises the amino acid sequence of SEQ ID NO:6 or a pharmaceutically acceptable salt thereof.

9. The method of claim 7, wherein the peptide comprises the amino acid sequence of SEQ ID NO:6.

10. The method of claim 7, wherein the cancer is a myeloma.

11. The method of claim 7, wherein the cancer is multiple myeloma.

12. An isolated peptide comprising the amino acid sequence of SEQ ID NO:6, or a pharmaceutically acceptable salt or variant thereof, wherein said variant has at least one of the following characteristics: said variant contains one or more hydroxyproline or hydroxylysine; said variant contains an organic acid or amide; said variant contains a C-terminal carboxylate; said variant is esterified; said variant is amidated; said variant has a modified N-terminal amino group; said variant has a side-chain modification or substitution selected from the group consisting of methylation, benzylation, t-butylation, tosylation, and alcoxycarbonylation; said variant has an N-acetyl group; said variant has a C-terminal amide group; or said variant has an amino acid selected from the group consisting of penicillamine, tetramethylene cysteine, pentamethylene cysteine, mercaptopropionic acid, pentamethylene-mercaptopropionic acid, 2-mercaptobenzene, 2-mercaptoaniline, 2-mercaptoproline, ornithine, diaminobutyric acid, aminoapidic acid, m-aminomethylbenzoic acid, and diaminopropionic acid.

13. An isolated peptide comprising the amino acid sequence of SEQ ID NO:6, or a pharmaceutically acceptable salt thereof.

14. An isolated peptide comprising the amino acid sequence of SEQ ID NO:6.

15. A pharmaceutical composition comprising an isolated peptide and a pharmaceutically acceptable carrier, wherein said peptide comprises the amino acid sequence of SEQ ID NO:6, or a pharmaceutically acceptable salt or variant thereof, wherein said variant has at least one of the following characteristics: said variant contains one or more hydroxyproline or hydroxylysine; said variant contains an organic acid or amide; said variant contains a C-terminal carboxylate; said variant is esterified; said variant is amidated; said variant has a modified N-terminal amino group; said variant has a side-chain modification or substitution selected from the group consisting of methylation, benzylation, t-butylation, tosylation, and alcoxycarbonylation; said variant has an N-acetyl group; said variant has a C-terminal amide group; or said variant has an amino acid selected from the group consisting of penicillamine, tetramethylene cysteine, pentamethylene cysteine, mercaptopropionic acid, pentamethylene-mercaptopropionic acid, 2-mercaptobenzene, 2-mercaptoaniline, 2-mercaptoproline, ornithine, diaminobutyric acid, aminoapidic acid, m-aminomethylbenzoic acid, and diaminopropionic acid.

16. The pharmaceutical composition of claim 15, wherein said peptide comprises the amino acid sequence of SEQ ID NO:6 or a pharmaceutically acceptable salt thereof.

17. The pharmaceutical composition of claim 15, wherein said peptide comprises the amino acid sequence of SEQ ID NO:6.

* * * * *

UNITED STATES PATENT AND TRADEMARK OFFICE
CERTIFICATE OF CORRECTION

PATENT NO.    : 6,812,003 B2
DATED         : November 2, 2004
INVENTOR(S)   : William S. Dalton, Jason S. Damiano and Anne E. Cress It is certified that error appears in the above-identified patent and that said Letters Patent is hereby corrected as shown below:

Title page,
Item [60], Related U.S. Application Data, "Mar. 1, 2001" should read -- March 1, 2000, --.

Column 2,
Line 8, "chemotherapeutic drug" should read -- chemotherapeutic drugs --.
Line 55, "J. Invest Dennaioi" should read -- J. Invest Dennatol --.
Line 58, "70:688,-1997" should read -- 70:688, 1997 --.

Column 3,
Line 19, "f a number" should read -- of a number --.

Column 4,
Lines 49-50, "on plastic, or FN" should read -- on plastic, BSA, or FN --.

Column 5,
Line 39, "of (he" should read -- of the --.

Column 6,
Lines 48-49, "maintained $6 \times 10^{-8}$" should read -- maintained in $6 \times 10^{-8}$ --.

Column 7,
Line 4, "the ($\alpha_4$" should read -- the $\alpha_4$ --.
Line 38, "calorimetric" should read -- colorimetric --.

Column 10,
Line 19, "alkoxycarbonylamino" should read -- alkoxycarbonylation --.
Line 22, "alkoxycarbonylamino" should read -- alkoxycarbonylation --.
Line 42, "of the amino" should read -- of the –amino --.

Column 15,
Line 49, "6.9.s.d." should read -- 6.9, s.d. --.

Column 17,
Line 16, "(n3)" should read -- (n=3) --.

Column 20,
Line 9, "L-glutamnine" should read -- L-glutamine --.

UNITED STATES PATENT AND TRADEMARK OFFICE
CERTIFICATE OF CORRECTION

PATENT NO. : 6,812,003 B2
DATED : November 2, 2004
INVENTOR(S) : William S. Dalton, Jason S. Damiano and Anne E. Cress It is certified that error appears in the above-identified patent and that said Letters Patent is hereby corrected as shown below:

Column 21,
Line 17, "P1D6, B3B11" should read -- P1D6, P4C10, B3B11 --.
Line 50, "(62.5 nM" should read -- (62.5mM --.

Column 23,
Line 23, "s.d.=70," should read -- s.d.=1.70, --.
Line 25, "to $3.4 \times 10^{-4}$M)" should read -- to $3.41 \times 10^{-4}$M) --.

Column 24,
Line 53, "⊕1," should read -- β1, --.

Column 25,
Line 27, "with a blocking" should read -- with α5 blocking --.
Line 39, "BCA/ABL" should read -- BCR/ABL --.
Line 59, "signaling K562" should read -- signaling. K562 --.

Column 26,
Line 1, "f an unknown" should read -- of an unknown --.

Column 28,
Line 14, "integrins implicated" should read -- integrins are implicated --.
Line 54, "cell to cycle" should read -- cell cycle --.
Line 54, "cells allowed" should read -- cells are allowed --.

Signed and Sealed this

Sixth Day of September, 2005

JON W. DUDAS
*Director of the United States Patent and Trademark Office*

UNITED STATES PATENT AND TRADEMARK OFFICE
CERTIFICATE OF CORRECTION

PATENT NO. : 6,812,003 B2  
DATED : November 2, 2004  
INVENTOR(S) : William S. Dalton, Jason S. Damiano and Anne E. Cress Page 1 of 1

It is certified that error appears in the above-identified patent and that said Letters Patent is hereby corrected as shown below:

<u>Column 28,</u>  
Line 30, "kviywkag" should read -- kmviywkag --.

Signed and Sealed this

Fourth Day of October, 2005

JON W. DUDAS  
*Director of the United States Patent and Trademark Office*

SEQUENCE LISTING

```
<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: BAX upstream primer

<400> SEQUENCE: 1
accaagaagc tgagcgagtg tctc                                           24

<210> SEQ ID NO 2
<211> LENGTH: 20
<212> TYPE: DNA
<213> ORGANISM: Artificial Sequence
<220> FEATURE:
<223> OTHER INFORMATION: BAX downstream primer

<400> SEQUENCE: 2
caatgtccag cccatgatgg                                                20
```

-continued

```
<210> SEQ ID NO 3
<211> LENGTH: 22
<212> TYPE: DNA
<213> ORGANISM: Artificial Sequence
<220> FEATURE:
<223> OTHER INFORMATION: upstream primer

<400> SEQUENCE: 3
atggctccca atgttagtgt gg                                          22

<210> SEQ ID NO 4
<211> LENGTH: 23
<212> TYPE: DNA
<213> ORGANISM: Artificial Sequence
<220> FEATURE:
<223> OTHER INFORMATION: downstream primer

<400> SEQUENCE: 4
cactggcttc ttttccactt tcc                                         23

<210> SEQ ID NO 5
<211> LENGTH: 9
<212> TYPE: PRT
<213> ORGANISM: Artificial Sequence
<220> FEATURE:
<223> OTHER INFORMATION: inhibitor of cell adhesion mediated drug
      resistance

<400> SEQUENCE: 5

Lys Met Val Ile Tyr Trp Lys Ala Gly
1               5

<210> SEQ ID NO 6
<211> LENGTH: 9
<212> TYPE: PRT
<213> ORGANISM: Artificial Sequence
<220> FEATURE:
<223> OTHER INFORMATION: RZ-3
<220> FEATURE:
<221> NAME/KEY: MISC_FEATURE
<222> LOCATION: (1)..(9)
<223> OTHER INFORMATION: Dextrorotatory amino acid

<400> SEQUENCE: 6

Lys Met Val Ile Tyr Trp Lys Ala Gly
1               5
```